US011648308B2

(12) United States Patent
Germaschewski et al.

(10) Patent No.: US 11,648,308 B2
(45) Date of Patent: May 16, 2023

(54) METHODS, REGIMENS, COMBINATIONS AND ANTAGONISTS

(71) Applicant: Kymab Limited, Cambridge (GB)

(72) Inventors: Volker Germaschewski, Cambridge (GB); Igor Theurl, Cambridge (GB); Martin Yateman, Cambridge (GB); Jasper Clube, Cambridge (GB); Steve Arkinstall, Cambridge (GB)

(73) Assignee: Kymab Limited, Cambridge (GB)

( * ) Notice: Subject to any disclaimer, the term of this patent is extended or adjusted under 35 U.S.C. 154(b) by 0 days.

(21) Appl. No.: 15/610,955

(22) Filed: Jun. 1, 2017

(65) Prior Publication Data
US 2017/0319689 A1  Nov. 9, 2017

Related U.S. Application Data

(63) Continuation of application No. PCT/GB2017/051208, filed on Apr. 28, 2017.

(30) Foreign Application Priority Data

May 3, 2016 (GB) ..................................... 1607705

(51) Int. Cl.
A61K 39/00 (2006.01)
A61K 38/18 (2006.01)
C07K 14/505 (2006.01)
C07K 16/22 (2006.01)
A61K 39/395 (2006.01)

(52) U.S. Cl.
CPC ...... *A61K 39/3955* (2013.01); *A61K 38/1816* (2013.01); *A61K 39/395* (2013.01); *C07K 16/22* (2013.01); *A61K 2039/507* (2013.01); *A61K 2039/545* (2013.01); *A61K 2300/00* (2013.01); *C07K 2317/21* (2013.01); *C07K 2317/34* (2013.01)

(58) Field of Classification Search
None
See application file for complete search history.

(56) References Cited

U.S. PATENT DOCUMENTS

| | | | |
|---|---|---|---|
| 4,675,187 A | 6/1987 | Konishi et al. | |
| 8,318,167 B2 | 11/2012 | Lin et al. | |
| 8,795,665 B2 | 8/2014 | Seo et al. | |
| 8,980,582 B2 | 3/2015 | Seo et al. | |
| 2005/0137329 A1* | 6/2005 | Holmes | C07K 14/001 525/54.1 |
| 2005/0272634 A1* | 12/2005 | Bahlmann | A61K 38/1816 514/1.9 |
| 2010/0136015 A1* | 6/2010 | Lin | C07K 16/22 424/139.1 |
| 2013/0059783 A1* | 3/2013 | Flygare | A61K 31/56 514/13.5 |
| 2014/0086919 A1 | 3/2014 | Lin et al. | |
| 2014/0199314 A1* | 7/2014 | Lin | C07K 16/22 424/139.1 |
| 2014/0309404 A1* | 10/2014 | Seo | C07K 16/22 530/387.9 |
| 2016/0176956 A1* | 6/2016 | Cong | A61K 38/1816 424/158.1 |
| 2022/0073598 A1 | 3/2022 | Germaschewski et al. | |

FOREIGN PATENT DOCUMENTS

| | | | |
|---|---|---|---|
| JP | 2012508764 A | 4/2012 | |
| JP | 2016501273 A | 1/2016 | |
| WO | 2008003103 A2 | 1/2008 | |
| WO | 2008003103 A3 | 4/2008 | |
| WO | 2010056981 A2 | 5/2010 | |
| WO | WO 2010-056981 | * | 5/2010 |
| WO | 2010056981 A3 | 9/2010 | |
| WO | 2011004192 A1 | 1/2011 | |
| WO | 2011158009 A1 | 12/2011 | |
| WO | 2013061098 A2 | 5/2013 | |
| WO | 2013061098 A3 | 6/2013 | |
| WO | 2014099391 A1 | 6/2014 | |
| WO | 2015040401 A1 | 3/2015 | |
| WO | 2015103072 A1 | 7/2015 | |
| WO | 2016098079 A2 | 6/2016 | |
| WO | WO-2016098079 A2 | 6/2016 | |
| WO | 2016098079 A3 | 8/2016 | |
| WO | 2017191437 A1 | 11/2017 | |
| WO | 2017216724 A1 | 12/2017 | |
| WO | 2020065252 A1 | 4/2020 | |

OTHER PUBLICATIONS

Flight, Monica. AstraZeneca bets on FibroGen's anaemia drug. Nature. vol. 12, p. 730 (Oct. 2013 ). (Year: 2013).*
Rivera et al. Animal Models of Anemia of Inflammation. Semin Hematol. October 46(4):351-357 (2009). (Year: 2009).*
Andriopoulos, B., Jr., et al., "BMP6 Is a Key Endogenous Regulator of Hepcidin Expression and Iron Metabolism," *Nature Genetics* 41(4):482-487, Nature Pub. Co., United States (2009).
Kidney Disease: Improving Global Outcomes (KDIGO) CKD-MBD Work Group, "KDIGO Clinical Practice Guideline for Anemia in Chronic Kidney Disease," *Kidney International Supplements* 2(4):279-335, KDIGO, United States (2012).
Kim, A., et al., "A Mouse Model of Anemia of Inflammation: Complex Pathogenesis With Partial Dependence on Hepcidin," *Blood* 123(8):1129-1136, American Society of Hematology, United States (2014).
Theurl, M., et al., "Hepcidin as a Predictive Factor and Therapeutic Target in Erythropoiesis-stimulating Agent Treatment for Anemia of Chronic Disease in Rats," *Haematologica* 99(9):1516-1524, Ferrata Storti Foundation, Italy (2014).

(Continued)

*Primary Examiner* — Elizabeth C. Kemmerer
*Assistant Examiner* — Regina M DeBerry
(74) *Attorney, Agent, or Firm* — Morrison & Foerster LLP

(57) ABSTRACT

The invention relates to treating or preventing anaemia in a subject, such as a mammal or human. In particular, the invention addresses moderate to severe anaemia. Additionally, the invention provides means for sparing administration of erythropoiesis stimulating agents (ESAs) to subjects.

20 Claims, 6 Drawing Sheets
Specification includes a Sequence Listing.

(56) References Cited

OTHER PUBLICATIONS

Thomas, D. Wayne et al., "Guideline for the Laboratory Diagnosis of Functional Iron Deficiency," Bristish Journal of Haematology, 2013, 161, pp. 639-648.
Amgen Inc. (Dec. 2013). "Epogen(R) (epoetin alfa) Injection, for Intravenous or Subcutaneous Use," 27 pages.
Amgen Inc. (Jul. 2015). "ARANESP(R) (darbepoetin alfa) Injection, for Intravenous or Subcutaneous Use," 25 pages.
Hayat, A. et al. (Jan. 1, 2008). "Erythropoietin Stimulating Agents in the Management of Anemia of Chronic Kidney Disease," Patient Preference and Adherence 2:195-200.
International Preliminary Report on Patentability, dated Nov. 6, 2018, for PCT Application No. PCT/GB2017/051208, filed Apr. 28, 2017, 6 pages.
International Search Report and Written Opinion, dated Aug. 23, 2017, for PCT Application No. PCT/GB2017/051208, filed Apr. 28, 2017, 10 pages.
Macciò, A. et al. (Jan. 1, 2012). "Management of Anemia of Inflammation in the Elderly," Anemia 2012 (563251):1-20.
Akchurin, O. et al. (2016, e-pub. Jul. 20, 20160. "Lack of Hepcidin Ameliorates Anemia and Improves Growth In An Adenine-Induced Mouse Model of Chronic Kidney Disease," Am. J. Physiol. Ren. Physiol. Ren. Physiol. 311:F877-F889.
Berger, S.L. (1987). "Isolation of Cytoplamic RNA: Ribonucleoside-Vanadyl Complexes," Methods in Enzymology 152:227-234.
Casanovas, G. et al. (Jan. 2, 2014). "A Multi-Scale 25 Model of Hepcidin Promoter Regulation Reveals Factors Controlling Systemic Iron Hemeostasis," PLoS Comput. Biol. 10(1):e1003421, 13 pages.
Chothia, C. et al. (1987). "Canonical Structures for the Hypervariable Regions of Immunoglobulins," J. Mol. Biol. 196:901-917.
DiGiammarino, E. et al. (2012). "Design and Generation of DVD-IgTM Molecules For Dual-Specific Targeting," Meth. Mo. Biol. 889:145-156.
Freshney, R.I. (2005). Culture of Animal Cells: A Manual of Basic Technique, 65th Edition, John Wiley & Sons, Inc. pp. 115-128. TOC, 12 pages.
Ganz, T. et al. (2011). "The Hepcidin-Ferroportin System as a Therapeutic Target in Anemias and Iron Overload Disorders," Hematology 2011:538-542.
International Preliminary Report on Patentability, dated Mar. 23, 2021, for PCT Application No. PCT/GB2019/052294, filed Aug. 15, 2019, 5 pages.
International Search Report and Written Opinion, dated Nov. 22, 2019, for PCT Application No. PCT/GB2019/052294, filed Aug. 15, 2019, 9 pages.
Kabat, E.A. et al. (1971). "Attempts to Locate Complementarity-Determining Residues in the Variable Positions of Light and Heavy Chains," Ann NY Acad Sci 190:382-391.
Kabat, E.A. et al. (1991). Sequences of Proteins of Immunological Interest, 5th Ed. Public Health Service, National Institutes of Health, Bethesda MD., Table of Contents, 21 pages.
Kautz, L. et al. (Oct. 16, 2014, e-pub. Sep. 5, 2014). "Erythroferrone Contributes to Recovery From Anemia of Inflammation," Blood 124(16):2569-2574.
Kim, S.Y. et al. (Nov. 19, 2015). "Recent Advances in Developing Inhibitors for Hypoxia-Inducible Factor Prolyl Hydroxylases and Their Therapeutic Implications," Molecules 20:20551-20568.
LaTour, C. et al. (2016, e-pub. Nov. 12, 2015). "Differing Impact of the Deletion of Hemochromatosis-Associated Molecules HFE and Trasferrin Receptor-2 on the Iron Phenotype of Mice Lacking Bone Morphogenetic Protein 6 or Hemojuvelin," Hepatology 63(1):126-137.
Lee, J.H. et al. (Sep. 25, 2015). "Antibodies to a Conformational Epitope on gp41 Neutralize HIV-1 by Destabilizing the Env Spike," Nature Communications 6:8167, 14 pages.
LeFranc, M.P. (Nov. 1, 1997). "Unique Database Numbering System for Immunogenetic Analysis," Immunol. Today 18(11):P509.

Mathis, G. (1995). "Probing Molecular Interactions with Homogeneous Techniques Based on Rare Earth Cryptates and Fluorescence Energy Transfer," Clinical Chemistry 41(9):1391-1397.
Mayeur, C. et al. (Apr. 3, 2014). "The Type I BMP Receptor Alk3 is Required for the Induction of Hepatic Hepcidin Gene Expression by Interleukin-6," Blood 123(14):2261-2268.
Nai, A. et al. (Feb. 12, 2015). "The Second Transferrin Receptor Regulates Red Blood Cell Production in Mice," Blood 125(7):1170-1179.
Nangaku, M. et al. (2007). "A Novel Class of Prolyl Hydroxylase Inhibitors Induces Angiogenesis and Exerts Organ Protection Against Ischemia," Arterioscler Thromb. Vasc. Biol. 27:2548-2554.
Niederfellner, G. et al. (Jul. 14, 2011). "Epitope Characterization and Crystal Structure of GA101 Provide Insights into the Molecular Basis for Type I/II Distinction of CD20 Antibodies," Blood 118(2):358-367.
Paul, W.E. ed., Fundamental Immunology: Second Edition, Raven Press, New York at (1989) pp. 332-337.
Poloznikov, A.A. et al. (Jan. 29, 20210. "HIF Prolyl Hydroxylase Inhibitors for COVID-19 Treatment: Pros and Cons," Frontiers in Pharmacology 11(621054):1-11.
Ramey, G. et al. (2010). "Hepcidin Targets Ferroportin for Degradation in Hepatocytes," Haematologica 95 (3):501-504.
Rudikoff, S. et al. (Mar. 1982). "Single Amino Acid Substitution Altering Antigen-Binding Specificity," Proc. Natl. Acad. Sci. USA 79:1979-1983.
Sambrook, J. et al. (2012). Molecular Cloning: A Laboratory Manual (4 ed.), Cold Spring Harbor Laboratory Press, Cold Spring Harbor, N.Y., USA, TOC, 34 pages.
Schluessener, H.J. et al. (1995). "Immunolocalization of BMP-6, A Novel RGF-β-Related Cytokind, in Normal and Atherosclerotic Smooth Muscle Cells," Atherosclerosis 113:153-156.
Selleck Chemical (2013). "HIF Inhibitors," Selleckchem.com, 4 pages.
Spiess, C. et al. (2015, e-pub. Jan. 27, 2015). "Alternative Molecular Formats and Therapeutic Applications for Bispecific Antibodies," Mol. Immunol. 67:95-106.
Steinbicker, A.U. et al. (Oct. 13, 2011, e-pub. Aug. 12, 2011). "Perturbation of Hepcidin Expression by BMP Type I Receptor Deletion Induces Iron Overload in Mice," Blood 118(15):4224-4230.
Suckau, D. et al. (Dec. 1990). "Molecular Epitope Identification by Limited Proteolysis of an Immobilized Antigen-Antibody Complex and Mass Spectrometric Peptide Mapping," Proceedings of the National Academy of Sciences 87:9848-9852.
Tegley, C.M. et al. (2008, e-pub. Jun. 13, 20080. "Discovery of Novel Hydroxy-Thiazoles as HIP-α Prolyl Hydroxylase Inhibitors: SAR, Synthesis, and Modeling Evaluation," Bioorganic & Medicinal Chemistry Letters 18:3925-3928.
The Human Protein Atlas (2021). Retrieved from internet www.proteinatlas.org/ENSG00000168509-5HFE2/cell#rna, last visited May 1, 2021, 1 page.
Theurl, I. et al. (Nov. 3, 2011, e-pub. Jul. 7, 2011). "Pharmacologic Inhibition of Hepcidin Expression Reverses Anemia of Chronic Inflammation in Rats," Blood 118(18):4977-4984, 16 pages.
Wang, R.-H. et al. (Dec. 2005). "A Role of SMAD4 in Iron Metabolism Through the Positive Regulation of Hepcidin Expression," Cell Metabolism 2(6):399-409.
Warshakoon, N.C. et al. (2006). "Design and Synthesis of a Series of Novel Pyrazolopyridines as HIF 1-α Prolyl Hydroxylase Inhibitors," Bioorganic & Medicinal Chemistry Letters 16:5687-5690.
Xia, Y. et al. (May 15, 2008). "Hemojuvelin Regulates Hepcidin Expression Via a Selective Subset of BMP LIgands and Receptors Independently of Neogenin," Blood 111(10):5195-5204.
Xu, J.L. et al. (Jul. 2000). "Diversity in the CDR3 Region of VH is Sufficient for Most Antibody Specificities," Immunity 13:37-45.
Yu, Z. et al. (May 31, 1993). "Recent Advances in Clinical hematology," Jinan University Press, pp. 83-84, with English Translation.
Yusa, K. et al. (Jan. 25, 2011). "A Hyperactive piggyBac Transposase for Mammalian Applications," Proc. Natl. Acad. Sci. U.S.A. 108(4):1531-1536.

* cited by examiner

METHODS, REGIMENS, COMBINATIONS AND ANTAGONISTS

CROSS-REFERENCE TO RELATED APPLICATIONS

This application is a continuation of International Appl. No. PCT/GB2017/051208, filed Apr. 28, 2017, which in turn claims priority to GB1607705.9, filed May 3, 2016, the contents of each of which is herein incorporated by reference in its entirety.

REFERENCE TO SEQUENCE LISTING

The content of the following submission on ASCII text file is incorporated herein by reference in its entirety: a computer readable form (CRF) of the Sequence Listing (file name: 165062000600SEQLIST.txt, date recorded: Sep. 16, 2021, size: 29,868 bytes).

FIELD OF THE INVENTION

The invention relates to treating or preventing anaemia in a subject, such as a mammal or human. In particular, the invention addresses moderate to severe anaemia. Additionally, the invention provides means for sparing administration of erythropoiesis stimulating agents (ESAs) to subjects.

BACKGROUND

Anaemia is a major disease impacting 25% of the global population, or more than 1.7 billion people, particularly pregnant women, neonates and children. More than 40% of anaemia reflect a malfunction in the homeostatic control of iron uptake, storage and recycling. This dysregulation is a consequence of a variety of chronic diseases including infection (e.g. HIV, hepatitis), inflammation (e.g. rheumatoid arthritis), cancer and kidney disease. The enormous impact of diseases causing dysregulation of iron homeostasis can be seen in the USA where, of 40 million adults of >65 years of age, 10% suffer from anaemia and ⅓ of these are caused by chronic disorders.

Standards of care focus on blood transfusions and treatments with ESAs such as EPO or Aranesp® (Amgen, Inc).

Anti-Bone Morphogenetic Protein 6 (BMP6) antagonists, such as antibodies, are being developed for use in a method of treating or preventing anaemia (see, eg, WO2016098079, US20160176956A1).

STATEMENT OF INVENTION

The invention is based on the inventors' realisation that a combination therapy of an anti-BMP6 antagonist and an ESA can be used to treat or prevent anaemia, particularly moderate to severe anaemia (ie, indicated by a blood haemoglobin of less than 9.5 g/dL).

The inventors have found such combination to be surprisingly efficacious for treating anaemia such as ACD (Anaemia of Chronic Disease), inflammation or infection and have demonstrated that the combination therapy can produce maintenance and elevation of blood haemoglobin concentration that is statistically significant versus use of an anti-BMP6 antibody alone. Furthermore, such effects are surprisingly durable over weeks (even after a single dose of administered anti-BMP6 antibody). We believe that this has not been shown or suggested previously in the art.

Additionally, the combination therapy of the invention is useful for ESA sparing anaemia therapy, ie, enabling ESA treatment with lower than standard doses of ESA. This is useful in view of potentially harmful side-effects of ESAs. The invention also may be useful for anaemia therapy in subjects that are refractory to ESAs or have poor response to standard ESA therapy. The invention usefully can maintain blood haemoglobin outside a moderate to severe anaemia range and/or prevent decrease of blood haemoglobin to such a range. The invention, thus, is useful for reducing the need for iron or blood transfusion therapy.

As exemplified herein, the invention is useful for anaemia therapy in inflammatory disease settings and microbial infection settings.

To this end, the invention provides the following configurations 1-13:—

1. A method of maintaining a blood haemoglobin level of at least 10 g/dL in a subject, the method comprising administering an anti-BMP6 antagonist and an erythropoiesis stimulating agent (ESA) to the subject.

2. A method of preventing the blood haemoglobin level of a subject from decreasing to less than 10 g/dL, the method comprising administering an anti-BMP6 antagonist and an erythropoiesis stimulating agent (ESA) to the subject.

3. A method of raising blood haemoglobin to a level of at least 10 g/dL in a subject suffering from anaemia, the method comprising administering an anti-BMP6 antagonist and an erythropoiesis stimulating agent (ESA) to the subject, wherein said anaemia is treated.

4. A method of treating or preventing moderate or severe anaemia in a subject, the method comprising administering an anti-BMP6 antagonist and an erythropoiesis stimulating agent (ESA) to the subject, wherein said anaemia is treated or prevented.

5. A method of treating or preventing anaemia in a subject suffering from an inflammatory disease or condition, the method comprising administering an anti-BMP6 antagonist and an erythropoiesis stimulating agent (ESA) to the subject, wherein said anaemia is treated or prevented.

6. A method of eliminating or reducing the need to administer iron or blood transfusion to a subject suffering from anaemia, the method comprising administering an anti-BMP6 antagonist and an erythropoiesis stimulating agent (ESA) to the subject, wherein said need is eliminated or reduced.

In an example, one, more or all of labile plasma iron (LPI), enhanced LPI (eLPI) and non-transferrin bound iron (NTBI) are reduced in the subject. In an example, one, more or all of labile plasma iron (LPI), enhanced LPI (eLPI) and non-transferrin bound iron (NTBI) are reduced in the subject.

7. A method of treating or preventing anaemia in a subject suffering from a microbial infection, the method comprising administering an anti-BMP6 antagonist and an erythropoiesis stimulating agent (ESA) to the subject.

8. A method of reducing administration of an erythropoiesis stimulating agent (ESA) to a subject suffering from anaemia for treating anaemia, the method comprising administering an anti-BMP6 antagonist and said ESA, wherein anaemia is treated in the subject.

9. A method of treating or reducing the risk of anaemia in a subject suffering from or at risk of anaemia, the method comprising administering an anti-BMP6 antagonist and a low dose of an erythropoiesis stimulating agent (ESA) to the subject, wherein anaemia is treated or the risk of anaemia is reduced in the subject.

10. A therapeutic regimen for treating or preventing anaemia in a subject suffering from or at risk of anaemia, the regimen comprising simultaneously or sequentially administering an anti-BMP6 antagonist and an ESA to the subject, wherein
   a. On day zero the antagonist is administered to the subject; and no later than day 7 (eg, on day 1) the ESA is administered to the subject; or
   b. On day zero the ESA is administered to the subject; and no later than day 7 (eg, on day 1) the antagonist is administered to the subject; or
   c. On day zero the antagonist and the ESA are simultaneously administered to the subject; or
   d. On day zero the subject has already received the ESA and on day zero the antagonist is administered to the subject; or
   e. On day zero the subject has already received the antagonist and on day zero the ESA is administered to the subject;
   whereby at day 14 or later the blood haemoglobin level is at least 10 g/dL in the subject, wherein said anaemia is treated or prevented.
11. A combination therapy for use in a method or regimen of any preceding claim for treating or preventing anaemia in a subject, the combination comprising
   a. An anti-BMP6 antagonist;
   b. An ESA; and
   c. Optionally instructions for use in the method or regimen.
12. An anti-BMP6 antagonist for use in a method or regimen of any preceding configuration for treating or preventing anaemia in a subject.
13. An anti-Bone Morphogenetic Protein 6 (BMP6) antagonist for use in a method of treating or preventing anaemia in a subject, the method comprising administering said anti-BMP6 antagonist and an erythropoiesis stimulating agent (ESA) to the subject, wherein said anaemia is treated or prevented.

In an aspect, the antagonist comprises or consists of an anti-BMP6 antibody or fragment, the method comprising
   (a) on an initial day ($D_0$) administering to the subject the anti-BMP6 antibody or fragment; and
   (b) in a period of at least 3 consecutive weeks, said period starting on $D_0$, administering a plurality of doses of an ESA wherein blood Hb concentration in said subject is elevated from a baseline concentration on $D_1$ for the entire duration of said period,
   such that:—
   (i) for the entire duration of said period Hb concentration is no lower than 100% of baseline Hb concentration; and during said period Hb concentration reaches at least 120% of baseline; and/or
   (ii) for the entire duration of said period Hb concentration is increased over baseline by at least 1 g/dl.

Further exemplification is provided below by way of worked experiments and data.

DETAILED DESCRIPTION

Figure 1:
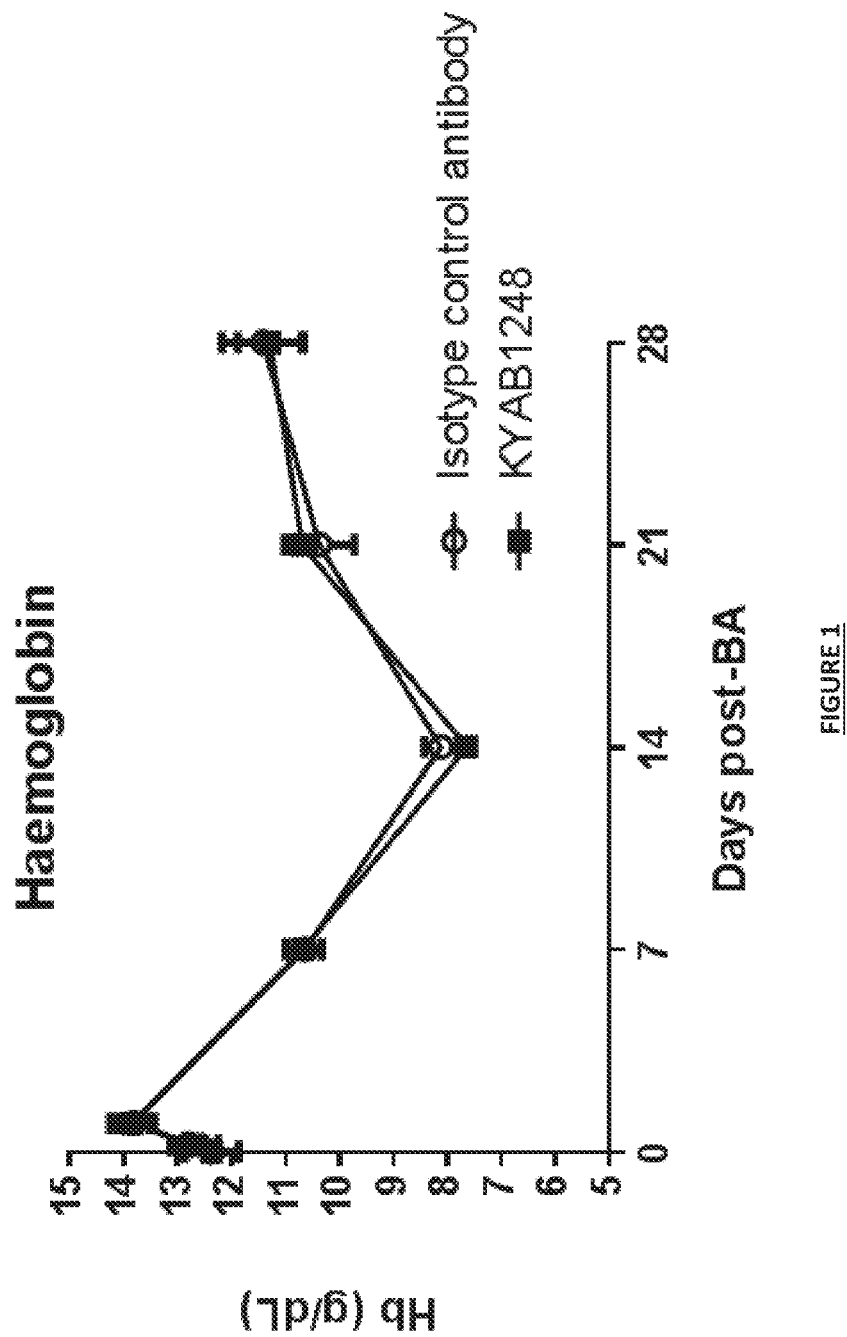
FIG. 1: Haemoglobin levels in murine Brucella model—antibody 10 mg/kg Day 0 & 6, no ESA.

Since iron is fundamental to all forms of life and has to be sourced from the environment, the availability and usage in the body is tightly controlled. A key regulator of iron homeostasis is a 25 amino acid peptide hormone called hepcidin. Hepcidin is produced by the liver and causes the main iron uptake and storage compartments, the duodenal enterocytes and macrophages, to retain iron by means of controlling expression of the iron transporter molecule ferroportin. Hepcidin itself is regulated by iron levels through a homeostatic control mechanism, following activation of the immune system during infection and/or inflammation as well as by erythropoiesis. Importantly, hepcidin levels are elevated in chronic inflammatory situations, infections and also certain cancers. Elevated hepcidin levels sequester iron in enterocytes, macrophages and hepatocytes thereby suppressing haemoglobin synthesis and erythropoiesis. This leads to anaemia despite the fact that iron storage levels are normal. Hepcidin gene expression is controlled by a soluble factor called BMP6 (bone morphogenetic protein 6). BMP6 is considered the master regulator, since in the absence of BMP6, cytokines alone (or other BMPs) are not able to overcome the deficit of a BMP6 signal. The inventors thus focused on BMP6 is a key drug target for controlling aberrant dysregulation of iron homeostasis in anaemia, eg, in anaemia of chronic disease (ACD).

BMP6 is a highly conserved soluble protein factor that is considered the "master" regulator of hepcidin production in mice and humans. Hence, administration of BMP6 to mice increases hepcidin levels and decreases blood and serum iron, while inhibitors of BMP6 do the opposite. In addition, knock-out of the mouse BMP6 gene or human mutations within the BMP6 pathway support a central role for BMP6 in controlling hepcidin and blood and serum iron levels. Furthermore, pre-clinical and clinical validation for targeting BMP6 comes from increasing available iron levels by administering an anti-BMP6 antibody to rodents or cynomolgus monkeys or BMP6 neutralization using HJV-Fc (FMX-8, Ferrumax Inc) in a Phase I study, respectively. Reference is made to Andriopoulos Jr. B, Corradini E, Xia Y, Faasse S A, Chen S, Grgurevic L, Knutson M D, Pietrangelo A, Vukicevic S, Lin H Y and Babitt. 2009. BMP-6 is a key endogenous regulator of hepcidin expression and iron metabolism. Nat. Genet. 41(4), 482-487; WO2016098079 and U.S. Pat. No. 8,980,582.

Aspects of the invention are as follows, and these aspects (and any un-numbered paragraphs) are combinable with any other configuration, example, feature, aspect or Clause of the invention as described herein; an antagonist (eg, anti-BMP6 antibody or fragment) or ESA of the invention can be provided for use in (or can be used in) a method in the following aspects:—
1. A method of maintaining a blood haemoglobin level of at least 10, 10.5, 11, 11.5, 12, 12.5 or 13 g/dL in a subject, the method comprising administering an anti-BMP6 antagonist and an erythropoiesis stimulating agent (ESA) to the subject.
   In an example, Hb level is no more than 11. 11.5 or 12 g/dl in the subject.
2. A method of preventing the blood haemoglobin level of a subject from decreasing to less than 10, 10.5, 11, 11.5, 12, 12.5 or 13/dL, the method comprising administering an anti-BMP6 antagonist and an erythropoiesis stimulating agent (ESA) to the subject.

3. A method of raising blood haemoglobin to a level of at least 10, 10.5, 11, 11.5, 12, 12.5 or 13 g/dL in a subject suffering from anaemia, the method comprising administering an anti-BMP6 antagonist and an erythropoiesis stimulating agent (ESA) to the subject, wherein said anaemia is treated.

In an example of any aspect, the subject is suffering from moderate or severe anaemia prior to administration of the BMP6 antagonist. An outcome of the method is, in one embodiment, that the subject does not have anaemia or has mild (and not moderate or severe) anaemia.

4. A method of treating or preventing moderate or severe anaemia in a subject, the method comprising administering an anti-BMP6 antagonist and an erythropoiesis stimulating agent (ESA) to the subject, wherein said anaemia is treated or prevented.

5. A method of treating or preventing anaemia in a subject suffering from an inflammatory disease or condition, the method comprising administering an anti-BMP6 antagonist and an erythropoiesis stimulating agent (ESA) to the subject, wherein said anaemia is treated or prevented.

In an example, the inflammatory disease or condition is selected from the group consisting of inflammation of microbial infection (eg, a bacterial infection) or rheumatoid arthritis. In an example, the anaemia is anaemia of inflammation (also known as anaemia of chronic disease, ACD).

6. A method of eliminating or reducing the need to administer iron or blood transfusion to a subject suffering from anaemia, the method comprising administering an anti-BMP6 antagonist and an erythropoiesis stimulating agent (ESA) to the subject, wherein said need is eliminated or reduced.

In an embodiment, the method reduces the dose (eg, weekly, fortnightly or monthly dose) or dosing frequency of iron.

7. A method of treating or preventing anaemia in a subject suffering from a microbial (eg, bacterial) infection, the method comprising administering an anti-BMP6 antagonist and an erythropoiesis stimulating agent (ESA) to the subject.

8. A method of reducing administration of an erythropoiesis stimulating agent (ESA) to a subject suffering from anaemia for treating anaemia, the method comprising administering an anti-BMP6 antagonist and said ESA, wherein anaemia is treated in the subject.

9. A method of treating or reducing the risk of anaemia in a subject suffering from or at risk of anaemia, the method comprising administering an anti-BMP6 antagonist and a low dose of an erythropoiesis stimulating agent (ESA) to the subject, wherein anaemia is treated or the risk of anaemia is reduced in the subject.

The dose is lower than a standard dose typically used to treat or reduce anaemia in a subject, eg, a human or adult human, such as a male or female. A typical dose for treatment or prophylaxis will be readily apparent to the skilled addressee. For example, see aspect 10.

Epogen is typically formulated in vials in multiple formulations. Single-dose vials, formulated with an isotonic sodium chloride/sodium citrate-buffered solution, are supplied in multiple strengths. Each 1 mL vial contains 2000, 3000, 4000, or 10,000 Units of epoetin alfa, Albumin (Human) (2.5 mg), citric acid (0.06 mg), sodium chloride (5.9 mg), and sodium citrate (5.8 mg) in Water for Injection, USP (pH 6.9±0.3). Single-dose 1 mL vials formulated with an isotonic sodium chloride/sodium phosphate buffer contain 40,000 Units of epoetin alfa albumin (human) (2.5 mg), citric acid (0.0068 mg), sodium chloride (5.8 mg), sodium citrate (0.7 mg), sodium phosphate dibasic anhydrate (1.8 mg), and sodium phosphate monobasic monohydrate (1.2 mg) in Water for Injection, USP (pH 6.9±0.3). Multidose, 2 mL vials contain 10,000 Units epoetin alfa, albumin (human) (2.5 mg), benzyl alcohol (1%), sodium chloride (8.2 mg), and sodium citrate (1.3 mg) per 1 mL Water for Injection, USP (pH 6.1±0.3). Multidose 1 mL vials contain 20,000 Units epoetin alfa, albumin (human) (2.5 mg), benzyl alcohol (1%), sodium chloride (8.2 mg), citric acid (0.11 mg), and sodium citrate (1.3 mg), per 1 mL in Water for Injection, USP (pH 6.1±0.3). In an example of the invention, the ESA is administered as one of these formulations.

10. The method of any preceding aspect, wherein the ESA is
   a. Epoetin alfa and is administered at a weekly dose of less than 1000, 1500, 2500, 5000, 11000, 18000, 34000 or 90000 units, optionally wherein the subject has previously received a weekly epoetin alfa treatment of <1500, 1500 to 2499, 2500 to 4999, 5000 to 10999, 11000 to 17999, 18000 to 33999, 34000 to 89999 or ≥90000 units respectively;
   b. darbepoetin alfa or Aranesp® and is administered at a weekly dose of less than 6.25, 10, 12.5, 20, 25, 40, 60, 100 or 200 mcg, optionally wherein the subject has previously received a weekly darbepoetin alfa or Aranesp® treatment of 6.25, 10, 12.5, 20, 25, 40, 60, 100 or 200 mcg respectively; or
   c. darbepoetin alfa or Aranesp® and is administered at a weekly dose of less than 6.25, 10, 20, 40, 60, 100 or 200 mcg, optionally wherein the subject has previously received a weekly Epoetin alfa treatment of 1500 to 2499, 2500 to 4999, 5000 to 10999, 11000 to 17999, 18000 to 33999, 34000 to 89999 or ≥90,000 units respectively.

11. The method of any preceding aspect, wherein the anti-BMP6 antagonist is an antibody and is administered at a total dose of no more than 30 mg/kg (eg, 0.1 to 30 mg/kg) such as every 1, 2 or 3 weeks, or every month, 2 months or 3 months. Administration can be IV or subcutaneous, eg, and the subject is a human such as a human adult.

12. A therapeutic regimen for treating or preventing anaemia in a subject suffering from or at risk of anaemia, the regimen comprising simultaneously or sequentially administering an anti-BMP6 antagonist and an ESA to the subject, wherein
   a. On day zero the antagonist is administered to the subject; and no later than day 56, 28, 14 or 7 (eg, on day 1, 6 or 7) the ESA is administered to the subject; or
   b. On day zero the ESA is administered to the subject; and no later than day 56, 28, 14 or 7 (eg, on day 1, 6 or 7) the antagonist is administered to the subject; or
   c. On day zero the antagonist and the ESA are simultaneously administered to the subject; or
   d. On day zero the subject has already received the ESA and on day zero the antagonist is administered to the subject; or
   e. On day zero the subject has already received the antagonist and on day zero the ESA is administered to the subject;
   whereby at day 14 or later (eg, at day 28, 56 or 70) the blood haemoglobin level is at least 10, 10.5, 11, 11.5, 12, 12.5 or 13 g/dL in the subject, wherein said anaemia is treated or prevented.

Optionally the antagonist is administered for a second time no later than day 7 (eg, the antagonist is administered on day 6).
13. The method or regimen of any preceding aspect, wherein the anti-BMP6 antagonist and ESA are administered to the subject no more than 7 days apart.
14. The method or regimen of any one of any preceding aspect, wherein the method or regimen maintains blood haemoglobin level in the subject at more than 10 g/dL in the subject.
15. The method or regimen of any preceding aspect, wherein the method or regimen maintains or raises blood haemoglobin level to at least 10 g/dL in the subject at least 13 or 14 days after the subject has received the anti-BMP6 antagonist and ESA.
16. The method or regimen of aspect 14 or 15, wherein the anti-BMP6 antagonist and ESA are administered to the subject no more than 1 day apart.
17. The method or regimen of any preceding aspect, wherein the anti-BMP6 antagonist and ESA are administered to the subject simultaneously.
18. The method or regimen of any preceding aspect, wherein the blood haemoglobin level of the subject is prevented from decreasing to less than 10, 10.5, 11, 11.5, 12, 12.5 or 13 g/dL (eg, at day 14).
19. The method or regimen of any preceding aspect, wherein the blood haemoglobin of the subject is raised to a level of at least 10, 10.5, 11, 11.5, 12, 12.5 or 13 g/dL (eg, at day 14).
20. The method or regimen of any preceding aspect, wherein moderate or severe anaemia is prevented in the subject (eg, at day 14).
21. The method or regimen of any preceding aspect, wherein the subject is suffering from
  a. an inflammatory disease or condition; or
  b. an infection;
  c. kidney disease;
  d. HIV or undergoing HIV treatment; or
  e. cancer; and
  anaemia is treated or prevented in the subject.
  In an example, the subject is suffering from HIV infection is HIV, hepatitis, rheumatoid arthritis, chronic kidney disease or end stage renal disease. For example, the infection is a gram-negative bacterial infection. For example, the infection is a gram-positive bacterial infection.
  HIV-infected humans treated with anti-HIV therapies may develop anaemia. Thus, the invention may be useful for treating or preventing anaemia in such patients. In an example, the method or regimen treats or prevents anaemia in a HIV-infected human administered with an anti-HIV therapy, eg, administered with <4200 mg/week zidovudine.
  Cancer patients treated with anti-cancer chemotherapy (eg, immunotherapy, eg, by administering an immune checkpoint inhibitor to the subject, eg, an anti-CTLA4, anti-PD-L1, anti-TIGIT, anti-ICOS or anti-PD1 antibody) may develop anaemia. Thus, the invention may be useful for treating or preventing anaemia in such patients. In an example, the method or regimen treats or prevents anaemia in a human suffering from a cancer. In the art, ESAs such as erythropoietin are typically administered to such patients at a dose of 150 units/kg IV or SC 3 times weekly initially; alternatively, 40,000 units SC once weekly until completion of chemotherapy course. In an example, the invention treats or prevents anaemia in a human cancer patient, wherein the ESA is administered to the human at less than 150 units/kg intravenously or subcutaneously 3 times weekly; or a total weekly dose of less than 450 units/kg; or less than 40,000 units subcutaneously weekly.
  ESA treatment is used in the art for the reduction of need for red blood cell (RBC) transfusions in patients, eg, in patients undergoing surgery. Thus, ESA treatment is used, for example, in human patients with perioperative haemoglobin>10 g/dL but ≤13 g/dL who are at high risk for perioperative blood loss from surgery, such as elective, noncardiac, nonvascular surgery. ESA is administered at 300 units/kg SC once daily for 15 consecutive days (10 days preceding surgery, day of surgery, 4 days following surgery); alternatively, 600 units/kg SC in 4 doses administered 21, 14, and 7 days before surgery and on day of surgery. In an example, the invention treats or prevents anaemia in a human surgery patient, wherein the ESA is administered to the human at less than 300 units/kg once daily for 15 consecutive days (10 days preceding surgery, day of surgery, 4 days following surgery); or less than a total 15 day dose of 4500 units/kg; or less than 600 units/kg in 3-5 or 4 doses, eg, administered 21, 14, and 7 days before surgery and on day of surgery.
22. The method of aspect 21, wherein moderate or severe anaemia is treated or prevented in the subject.
23. The method or regimen of any preceding aspect, wherein the subject is a mammal.
24. A combination therapy for use in a method or regimen of any preceding aspect for treating or preventing anaemia in a subject, the combination comprising
  a. An anti-BMP6 antagonist;
  b. An ESA; and
  c. Optionally instructions for use in the method or regimen.
25. An anti-BMP6 antagonist for use in a method or regimen of any preceding aspect for treating or preventing anaemia in a subject.
26. The combination of aspect 24 or the antagonist of aspect 25, for treating or preventing moderate or severe anaemia.
27. The combination of antagonist of any one of aspects 24 to 26 in combination with an anti-inflammatory agent.
28. The method, regimen, combination or antagonist of any preceding aspect, wherein the antagonist comprises an anti-BMP6 antibody binding site, eg, wherein the antagonist is an antibody or anti-BMP6 trap.
  In an example, the trap comprises a human BMP6 receptor domain fused to a human antibody Fc region. In an embodiment, the Fc comprises a human gamma-1 or -4 heavy chain constant region.
29. The method, regimen, combination or antagonist of any preceding aspect, wherein the ESA is an erythropoietin.
30. The method or regimen of any one of aspects 1 to 23, 28 and 29 wherein an anti-inflammatory agent is administered to the subject.

In an example, the invention uses an anti-BMP6 monoclonal antibody (mAb) for mobilising endogenous iron stores and increasing haemoglobin synthesis and optionally also erythropoiesis. The invention, in one aspect, may reduce the need for simultaneous and prevalent use of intravenous iron or blood transfusions in ACD patients. Additionally or alternatively, the invention may reduce the dose for the underlying standard of care treatment with ESA (eg, EPO) or render ESA (eg, EPO)-non responsive patients (or those with low response) responsive to ESA co-administration with an anti-BMP6 antagonist. Additionally or alternatively, the invention may treat or prevent anaemia in patients whose anaemia is refractory or non-responsive to ESA standard of care. ESAs may be contraindicated in patients that have uncontrolled high blood pressure, or have had pure red cell aplasia (PRCA, a type of anemia) caused by receiving an ESA (eg, darbepoetin alfa, such as Aranesp®, or eg, epoetin alfa, such as Epogen® or Procrit®).

Thus, in one embodiment of the invention the subject (eg, a human) is
  i. Refractory or non-responsive to an ESA (eg, darbepoetin alfa or epoetin alfa);
  ii. Suffers from or has suffered from high blood pressure (eg, uncontrolled high blood pressure); or
  iii. Suffers from or has suffered from pure red cell aplasia (eg, caused by receiving an ESA, such as darbepoetin alfa or epoetin alfa).

"Refractory" in relation to drug treatment, such as ESA treatment will be readily apparent to the skilled addressee, and for example means that the subject is ESA-resistant or a low responder to the ESA (ie, has a less than average response) and is not effectively treated for anaemia by the standard of care using an ESA.

ESAs are typically used to maintain haemoglobin at the lowest level that both minimises transfusions and best meets a patient's needs. As explained above, the invention in its various configurations, aspects, examples and embodiments is useful for ESA sparing anaemia therapy, ie, enabling ESA treatment with lower than standard doses of ESA. This is useful in view of potentially harmful side-effects of ESAs. Tables 1-4 provide relevant information in this respect.

TABLE 1

| Aranesp ® dosing information |
|---|
| Usual Adult Dose of Aranesp for Anaemia Associated with Chronic Renal Failure: |
| Chronic Kidney Disease (CKD) Patients Not on Dialysis: |
| Initial dose: 0.45 mcg/kg IV or subcutaneously once every 4 weeks as appropriate |
| Comments: |
| Initiate treatment only when haemoglobin is less than 10 g/dL, rate of haemoglobin decline indicates likelihood of requiring RBC transfusion, and reducing risk of alloimmunisation and/or other RBC transfusion-related risks is a goal. |
| CKD Patients on Dialysis: |
| Initial dose: 0.45 mcg/kg IV or subcutaneously once a week or 0.75 mcg/kg once every 2 weeks as appropriate |
| Comments: |
| Initiate treatment when haemoglobin is less than 10 g/dL. |
| IV route is recommended for patients on hemodialysis. |
| Usual Adult Dose of Aranesp for Anemia Associated with Chemotherapy: |
| Initial dose: 2.25 mcg/kg subcutaneously once a week or 500 mcg subcutaneously once every 3 weeks |
| Duration of therapy: Until completion of chemotherapy course |
| Comments: |
| Initiate treatment if haemoglobin is less than 10 g/dL and a minimum of 2 additional months of chemotherapy is planned. |
| Use the lowest dose necessary to avoid RBC transfusions. |
| Use: Treatment of anemia in patients with non-myeloid malignancies where anemia is due to the effect of concomitant myelosuppressive chemotherapy. |
| Usual Pediatric Dose of Aranesp for Anemia Associated with Chronic Renal Failure: |
| Less than 18 Years: |
| Initial dose: |
| Chronic Kidney Disease (CKD) Patients Not on Dialysis: 0.45 mcg/kg IV or subcutaneously once a week or 0.75 mcg/kg once every 2 weeks |
| CKD Patients on Dialysis: 0.45 mcg/kg IV or subcutaneously once a week |
| Comments: |
| Initiate treatment when haemoglobin is less than 10 g/dL. |
| mcg = micrograms |

In an example, the subject is a Chronic Kidney Disease (CKD) patient not on dialysis. In an example, the subject is a Chronic Kidney Disease (CKD) patient on dialysis. In an example, the subject is a chemotherapy patient (eg, receiving or having received chemotherapy treatment for cancer).

TABLE 2

| Aranesp ® Side Effects |
|---|
| In addition to its needed effects, some unwanted effects may be caused by darbepoetin alfa (the active ingredient contained in Aranesp). |
| More common |
|     Abdominal or stomach pain |
|     accumulation of pus |
|     arm, back, or jaw pain |
|     blurred vision |
|     breathing problems (irregular, noisy, or trouble when resting) |
|     chest pain, discomfort, tightness, or heaviness |
|     chills |
|     confusion |
|     cough producing mucus |

TABLE 2-continued

Aranesp ® Side Effects decrease in the amount of urine
    diarrhea
    dilated neck veins
    dizziness, fainting, or lightheadedness
    dry mouth
    fast, slow, or irregular heartbeat
    fatigue or tiredness (extreme or unusual)
    fever
    headache
    nausea
    pain, tenderness, swelling, or warmth over injection site
    pounding in the ears
    rapid breathing
    rapid or pounding pulse
    shortness of breath
    skin discoloration at the injection site
    sunken eyes
    sweating
    swelling of the ankles, face, fingers, feet, hands, or lower legs
    thirst
    trouble with breathing
    unconsciousness
    vomiting
    weight gain
    wheezing
    wrinkled skin
Less common
    Anxiety
    convulsions
    difficulty with speaking (slow speech or unable to speak)
    double vision
    trouble with thinking
    trouble with walking
    unable to move the arms, legs, or face muscles (including numbness and tingling)
Rare
    Fever and sore throat
    hives
    itching
    pale skin
    skin rash
    unusual tiredness or weakness
Some of the side effects that can occur with darbepoetin alfa may not need medical attention. As
your body adjusts to the medicine during treatment these side effects may go away. Your health
care professional may also be able to tell you about ways to reduce or prevent some of these side
effects. If any of the following side effects continue, are bothersome or if you have any questions
about them, check with your health care professional:
More common
    Constipation
    general feeling of discomfort or illness
    lack or loss of strength
    loss of appetite
    itching
    pale skin
    skin rash
    unusual tiredness or weakness
Applies to darbepoetin alfa: injectable solution
General
The most common adverse reactions in patients with chronic kidney disease (CKD) were
hypertension, dyspnea, peripheral edema, cough, and procedural hypotension. The most common
adverse reactions in cancer patients receiving chemotherapy were abdominal pain, edema, and
thrombovascular events.
Gastrointestinal
Very common (10% or more): Nausea (up to 38%), vomiting (up to 27%), diarrhea (up to 20%),
constipation (up to 19%), abdominal pain (up to 16%)
Common (1% to 10%): Dyspepsia
Other
Very common (10% or more): Fatigue (up to 32%), fever (up to 19%), peripheral edema (up to
17%), asthenia (up to 16%), edema (up to 12.8%), procedural hypotension (10%), chest pain (up to
10%)
Common (1% to 10%): Death, influenza-like symptoms, fluid overload, fall, contusion, pain,
arteriovenous graft thrombosis
Cardiovascular
Very common (10% or more): Hypertension (up to 31%), hypotension (up to 22%)
Common (1% to 10%): Myocardial infarction, thrombotic events, angina pectoris
Frequency not reported: Arrhythmia, thromboembolism, thrombosis, thrombophlebitis
Musculoskeletal
Very common (10% or more): Myalgia (up to 20%), back pain (14%), arthralgia (up to 13%), limb
pain (up to 11%)

TABLE 2-continued

Aranesp ® Side Effects

Common (1% to 10%): Skeletal pain
Respiratory
Very common (10% or more): Dyspnea (up to 20%), upper respiratory infection (up to 14%), cough
(up to 12%), nasopharyngitis (11%)
Common (1% to 10%): Bronchitis, sinusitis, sore throat, pulmonary embolism
Nervous system
Very common (10% or more): Headache (up to 16%), dizziness (up to 14%)
Common (1% to 10%): Cerebrovascular accident/transient ischemic attack, convulsions,
paresthesia, hypoesthesia, cerebrovascular disorders, stroke
Frequency not reported: Somnolence
Genitourinary
Very common (10% or more): Urinary tract infection (15%)
Renal
Very common (10% or more): Chronic renal failure (15%)
Metabolic
Very common (10% or more): Hypoglycemia (14%)
Psychiatric
Very common (10% or more): Insomnia (11%)
Common (1% to 10%): Depression, anxiety
Dermatologic
Common (1% to 10%): Pruritus, cellulitis, rash, skin ulcer, alopecia
Frequency not reported: Angioedema, urticaria
Local
Common (1% to 10%): Injection site pain, access hemorrhage, access infection, vascular access
thrombosis, vascular access complications
Hematologic
Common (1% to 10%): Granulocytopenia
Frequency not reported: Anemia, pure red cell aplasia associated with neutralizing antibodies to
erythropoietin
Oncologic
Common (1% to 10%): Metastatic neoplasm
immunologic
Frequency not reported: Serious allergic reaction, hypersensitivity reaction, anaphylactic reaction
References:
1. Cerner Multum, Inc. "Australian Product Information.";
2. "Product Information. Aranesp (darbepoetin alfa)." Amgen, Thousand Oaks, CA;
3. Cerner Multum, Inc. "UK Summary of Product Characteristics,"

In an embodiment, the treatment or prophylaxis of the invention reduces in the subject the incidence or risk of one or more side effects listed in Table 2, eg, one or more of the "common", "more common" or "very common" side effects.

In an aspect, the invention provides a method of reduced side-effect ESA therapy of a subject suffering from or at risk of anaemia, the method comprising administering an anti-BMP6 antagonist and an erythropoiesis stimulating agent (ESA) to the subject, wherein said anaemia is treated or prevented. Optionally, the incidence or risk of one or more ESA side effects listed in Table 2 (eg, one or more of the "common", "more common" or "very common" side effects) is reduced. In an example, the therapy is anaemia treatment. In an example, the therapy is anaemia prophylaxis. In an example, the anaemia is moderate or severe anaemia.

In an embodiment, the treatment or prophylaxis of the invention reduces in the subject the incidence or risk of one or more side effects listed in Table 3, eg, shortened overall survival and/or increased risk of tumour progression or recurrence wherein the subject is a breast, non-small cell lung, head and neck, lymphoid, and cervical cancer patient; or a cardiovascular or thromboembolic reaction, such as stroke.

In an aspect, the invention provides a method of reduced side-effect ESA therapy of a subject suffering from or at risk of anaemia, the method comprising administering an anti-BMP6 antagonist and an erythropoiesis stimulating agent (ESA) to the subject, wherein said anaemia is treated or prevented. Optionally, the incidence or risk of one or more ESA side effects listed in Table 3 (eg, shortened overall survival and/or increased risk of tumour progression or recurrence wherein the subject is a breast, non-small cell

TABLE 3

Aranesp ® US Boxed Warnings

CANCER: ESAs shortened overall survival and/or increased the risk of tumor progression or
recurrence in clinical studies of patients with breast, non-small cell lung, head and neck, lymphoid,
and cervical cancers. Because of these risks, prescribers and hospitals must enroll in and comply
with the ESA APPRISE Oncology Program to prescribe and/or dispense this drug to patients with
cancer. To enroll in the ESA APPRISE Oncology Program, visit www.esa-apprise.com or call 1-866-
284-8089 for further assistance. To decrease these risks, as well as the risk of serious
cardiovascular and thromboembolic reactions, use the lowest dose needed to avoid RBC
transfusions. Use ESAs only for anemia from myelosuppressive chemotherapy. ESAs are not
indicated for patients receiving myelosuppressive chemotherapy when the anticipated outcome is
cure. Discontinue following the completion of a chemotherapy course.

lung, head and neck, lymphoid, and cervical cancer patient; or a cardiovascular or thromboembolic reaction, such as stroke) is reduced. In an example, the therapy is anaemia treatment. In an example, the therapy is anaemia prophylaxis. In an example, the anaemia is moderate anaemia. In an example, the anaemia is moderate to severe anaemia. In an example, the anaemia is severe anaemia. In an example, the anaemia in the invention is anaemia from myelosuppressive chemotherapy.

TABLE 4

Estimated Aranesp Starting Doses (mcg/week) for Patients with CKD on Dialysis Based on Previous Epoetin alfa Dose (Units/week)

| Previous Weekly Epoetin alfa Dose (Units/week) | Aranesp Dose (mcg/week) | |
|---|---|---|
| | Adult | Paediatric |
| <1,500 | 6.25 | * |
| 1,500 to 2,499 | 6.25 | 6.25 |
| 2,500 to 4,999 | 12.5 | 10 |
| 5,000 to 10,999 | 25 | 20 |
| 11,000 to 17,999 | 40 | 40 |
| 18,000 to 33,999 | 60 | 60 |
| 34,000 to 89,999 | 100 | 100 |
| ≥90,000 | 200 | 200 |

* For paediatric patients receiving a weekly epoetin alfa dose of <1,500 Units/week, the available data are insufficient to determine an Aranesp conversion dose.

Aspects of the invention provide (i) and (ii)
(i) A method of reducing administration of an erythropoiesis stimulating agent (ESA) to a subject suffering from anaemia for treating anaemia, the method comprising administering an anti-BMP6 antagonist and said ESA, wherein anaemia is treated in the subject.
(ii) A method of treating or reducing the risk of anaemia in a subject suffering from or at risk of anaemia, the method comprising administering an anti-BMP6 antagonist and a low dose of an erythropoiesis stimulating agent (ESA) to the subject, wherein anaemia is treated or the risk of anaemia is reduced in the subject.

In examples of these aspects the ESA is
a. Epoetin alfa and is administered at a weekly dose of less than 1000, 1500, 2500, 5000, 11000, 18000, 34000 or 90000 units, optionally wherein the subject has previously received a weekly epoetin alfa treatment of <1500, 1500 to 2499, 2500 to 4999, 5000 to 10999, 11000 to 17999, 18000 to 33999, 34000 to 89999 or ≥90000 units respectively;
b. darbepoetin alfa or Aranesp® and is administered at a weekly dose of less than 6.25, 10, 12.5, 20, 25, 40, 60, 100 or 200 mcg, optionally wherein the subject has previously received a weekly darbepoetin alfa or Aranesp® treatment of 6.25, 10, 12.5, 20, 25, 40, 60, 100 or 200 mcg respectively; or
c. darbepoetin alfa or Aranesp® and is administered at a weekly dose of less than 6.25, 10, 20, 40, 60, 100 or 200 mcg, optionally wherein the subject has previously received a weekly Epoetin alfa treatment of 1500 to 2499, 2500 to 4999, 5000 to 10999, 11000 to 17999, 18000 to 33999, 34000 to 89999 or ≥90,000 units respectively.

In examples the ESA is
(i) Epoetin alfa and is administered at a weekly dose in the range from 3000 to 30000 units; or
(ii) darbepoetin alfa or Aranesp® and is administered at a weekly dose in the range from 15 to 100 mcg; and wherein the subject is a human, eg, an adult human.

In an example, the blood haemoglobin is raised to or maintained at a level of more than 10 g/dL.

In an example, the subject is an adult human. In an example, the subject is a paediatric human. In an example, the subject is a human CKD patient on dialysis treatment. In an example, the subject is a human having end-stage renal disease.

A therapeutically or prophylactically effective amount of the antagonist and ESA are administered to the subject in the methods of the invention. In an example, the anti-BMP6 antagonist and ESA are administered to the subject no more than 10, 14, 21 or 28 days apart. For example, the anti-BMP6 antagonist and ESA are administered to the subject no more than 1 or 2 months apart.

Examples of Erythropoiesis-Stimulating Agents (ESAs) are epoetin alfa, Epogen®, Dynepo®, Eprex®, erythropoietin, Darbepoetin alfa, Aranesp®, Epoetin beta, NeoRecormon®, methoxy polyethylene glycol-epoetin beta, Mircera® and Procrit®. In an embodiment, the ESA of the invention is any one of these or a combination of two or more of these.

In an example, the ESA comprises or consists of recombinant erythropoietin, eg, selected from the following table. Erythropoietin has a variety of glycosylation patterns giving rise to alpha, beta, delta, and omega forms:

TABLE 5

Example Erythropoietins

| | |
|---|---|
| epoetin alfa: | epoetin zeta (biosimilar forms |
| Darbepoetin (Aranesp ™) | for epoetin alpha): |
| Epocept ™ (Lupin pharma) | Silapo ™ (from Stada) |
| Nanokine ™ (Nanogen | Retacrit ™ (from Hospira) |
| Pharmaceutical biotechnology, | Miscellaneous: |
| Vietnam) | Epocept ™, made by Lupin |
| Epofit ™ (Intas pharma) | Pharmaceuticals |
| Epogen ™, made by Amgen | EPOTrust ™, made by |
| Epogin ™ | Panacea Biotec Ltd |
| Eprex ™, made by Janssen-Cilag | Erypro Safe ™, made by |
| Binocrit ™, made by Sandoz | Biocon Ltd. |
| Procrit ™ | Repoitin ™, made by |
| epoetin beta: | Serum Institute of India |
| NeoRecormon ™, made | Limited |
| by Hoffmann-LaRoche | Vintor ™, made by Emcure |
| Recormon ™ | Pharmaceuticals |
| Methoxy polyethylene glycol- | Epofit ™, made by Intas |
| epoetin beta (Mircera ™) by | pharma |
| Roche epoetin delta: | Erykine ™, made by Intas |
| Dynepo ™ trademark name for an | Biopharmaceutica |
| erythropoiesis stimulating protein, | Wepox ™, made by |
| by Shire plc | Wockhardt Biotech |
| epoetin omega: | Espogenm ™, made by LG |
| Epomax ™ | life sciences. |
| | ReliPoietin ™, made by |
| | Reliance Life Sciences |
| | Shanpoietin ™, made by |
| | Shantha Biotechnics Ltd |
| | Zyrop ™, made by Cadila |
| | Healthcare Ltd. |
| | EPIAO ™ (rHuEPO), |
| | made by Shenyang |
| | Sunshine Pharmaceutical |
| | Co., LTD. China |
| | Cinnapoietin ™, made by |
| | CinnaGen |
| | biopharmaceutical Iran. |

In an example, the ESA of the invention is selected from the group consisting of an alpha, beta, delta, zeta and omega form.

In an example, the ESA is a hypoxia-inducible factor prolyl-hydroxylase (HIF-PH) inhibitor, eg, roxadustat or FG-4592. HIF is the primary regulator of the production of red blood cells (RBCs) in the body and a potentially novel mechanism of treating anaemia. This novel mechanism of action is referred to as hypoxia inducible factor-prolyl hydroxylase (HIF-PH) inhibitors. HIF-PH inhibitors act by simulating the body's natural response to anaemia. This allows a controlled, adaptive stimulation of the erythropoietic system in the body. This activation of the whole system results in both increased red blood cell (RBC) production and improved stabilization of the bone marrow's iron supply, which ensures the proper incorporation of iron into haemoglobin necessary for such RBC production. This adaptive simulation is very similar to the natural response that is induced when a person ascends in altitude. At higher altitudes, low levels of oxygen circulating in the bloodstream lead to reduced HIF-PH activity in relevant cells in the kidney and liver. The reduced HIF-PH activity stabilizes and increases intracellular levels of proteins HIF1α and HIF2α (referred to as HIFα collectively). For most cells the stabilization of HIF2α is greater than that of HIF1α, which ultimately leads to an increase in erythropoietin (EPO) secretion and a subsequent increase in RBC production. HIF-PH inhibitors work by blocking the effect of the prolyl hydroxylase enzymes, which promote the breakdown of HIFα proteins. As the breakdown is inhibited, the level of these HIFα proteins increases in cells. These HIFs are the primary protein mediators that enable the body and all of its individual cells to adapt to changes in levels of oxygen. Both HIFα proteins are consistently produced and their levels in cells are adjusted by the activity of the HIF-PH enzymes, which target the HIFα proteins for degradation. HIF1α helps cells survive under very low oxygen conditions, whereas HIF2α helps cells and the body to adapt to modest changes in oxygen, such that would occur with a change in altitude from sea level to up to 7500 feet. When HIFα is stabilized, it travels to the nucleus of the cell, where it binds to the protein HIFβ. When bound together, they induce the genetic signal for the production of EPO and several other proteins. The HIF-PH inhibitors increase HIFα levels much in the same way that a reduction in oxygen increases HIFα levels by inhibiting the HIF-PH enzymes in the body. With continued stabilisation of HIFα (either by staying at higher altitude or by daily dosing of the HIF-PH inhibitor), the level of haemoglobin and RBCs will rise in order to increase the amount of oxygen circulating in the blood.

In an example, the antagonist is instead an anti-BMP6 antibody or an anti-BMP6 antibody binding fragment. An example of an anti-BMP6 antibody is MAB507, that is commercially available from R&D Systems (Monoclonal Mouse IgG2B, Clone #74219). Other suitable antibodies are disclosed in U.S. Pat. No. 8,980,582, WO2016098079 and US20160176956A1 the disclosure of which (and explicitly the sequences of antibodies, variable regions and CDRs therein) are incorporated herein by reference for possible use in the present invention as an anti-BMP6 antagonist.

In an embodiment, the antagonist comprises or consists of an antibody, or antigen-binding fragment thereof, that binds to human BMP-6 (SEQ ID NO: 1), comprising a light chain variable region (LCVR) and a heavy chain variable region (HCVR), wherein the LCVR comprises the complementarity determining regions (CDRs) LCDR1, LCDR2, and LCDR3, and the HCVR comprises the CDRs HCDR1, HCDR2, and HCDR3, wherein the LCDR1 is the polypeptide of SEQ ID NO: 2, the LCDR2 is the polypeptide of SEQ ID NO: 3, the LCDR3 is the polypeptide of SEQ ID NO: 4, the HCDR1 is the polypeptide of SEQ ID NO: 5, the HCDR2 is the polypeptide of SEQ ID NO: 6 or SEQ ID NO: 7, and the HCDR3 is the polypeptide of SEQ ID NO: 8. The SEQ ID NOs are those disclosed in U.S. Pat. No. 8,980,582, and these sequences are explicitly incorporated herein by reference for possible use in the present invention and for possible inclusion in one or more claims herein.

In an embodiment, the antagonist comprises or consists of an antibody, or antigen-binding fragment thereof, that binds to human BMP-6 (SEQ ID NO: 1), comprising a light chain variable region (LCVR) and a heavy chain variable region (HCVR), wherein the LCVR comprises the complementarity determining regions (CDRs) LCDR1, LCDR2, and LCDR3, and the HCVR comprises the CDRs HCDR1, HCDR2, and HCDR3, wherein the LCDR1 is the polypeptide of SEQ ID NO: 2, the LCDR2 is the polypeptide of SEQ ID NO: 3, the LCDR3 is the polypeptide of SEQ ID NO: 4, the HCDR1 is the polypeptide of SEQ ID NO: 5, the HCDR2 is the polypeptide of SEQ ID NO: 6, and the HCDR3 is the polypeptide of SEQ ID NO: 8. The SEQ ID NOs are those disclosed in U.S. Pat. No. 8,980,582, and these sequences are explicitly incorporated herein by reference for possible use in the present invention and for possible inclusion in one or more claims herein.

In an embodiment, the antagonist comprises or consists of an antibody, or antigen-binding fragment thereof, that binds to human BMP-6 (SEQ ID NO: 1), comprising a light chain variable region (LCVR) and a heavy chain variable region (HCVR), wherein the LCVR comprises the complementarity determining regions (CDRs) LCDR1, LCDR2, and LCDR3, and the HCVR comprises the CDRs HCDR1, HCDR2, and HCDR3, wherein the LCDR1 is the polypeptide of SEQ ID NO: 2, the LCDR2 is the polypeptide of SEQ ID NO: 3, the LCDR3 is the polypeptide of SEQ ID NO: 4, the HCDR1 is the polypeptide of SEQ ID NO: 5, the HCDR2 is the polypeptide of SEQ ID NO: 7, and the HCDR3 is the polypeptide of SEQ ID NO: 8. The SEQ ID NOs are those disclosed in U.S. Pat. No. 8,980,582, and these sequences are explicitly incorporated herein by reference for possible use in the present invention and for possible inclusion in one or more claims herein.

In an embodiment, the antagonist comprises or consists of an antibody, or antigen-binding fragment thereof, that binds to human BMP-6 (SEQ ID NO: 1), comprising an LCVR and an HCVR, wherein the LCVR is the polypeptide of SEQ ID NO: 9, and the HCVR is the polypeptide of SEQ ID NO: 10 or SEQ ID NO: 11. In a further embodiment, the antagonist comprises or consists of an antibody, or antigen-binding fragment thereof, that binds to human BMP-6 (SEQ ID NO: 1), comprising an LCVR and an HCVR, wherein the LCVR is the polypeptide of SEQ ID NO: 9, and the HCVR is the polypeptide of SEQ ID NO: 10. In another embodiment, the antagonist comprises or consists of an antibody, or antigen-binding fragment thereof, that binds to human BMP-6 (SEQ ID NO: 1), comprising an LCVR and an HCVR, wherein the LCVR is the polypeptide of SEQ ID NO: 9, and the HCVR is the polypeptide of SEQ ID NO: 11. The SEQ ID NOs are those disclosed in U.S. Pat. No. 8,980,582, and these sequences are explicitly incorporated herein by reference for possible use in the present invention and for possible inclusion in one or more claims herein.

In an embodiment, the antagonist comprises or consists of an antibody that binds to human BMP-6 (SEQ ID NO: 1), comprising an LCVR and an HCVR, wherein the LCVR is the polypeptide of SEQ ID NO: 9, and the HCVR is the polypeptide of SEQ ID NO: 10 or SEQ ID NO: 11. In a further embodiment, the present invention provides an antibody that binds to human BMP-6 (SEQ ID NO: 1), comprising an LCVR and an HCVR, wherein the LCVR is the polypeptide of SEQ ID NO: 9, and the HCVR is the polypeptide of SEQ ID NO: 10. In another embodiment, the antagonist comprises or consists of an antibody that binds to human BMP-6 (SEQ ID NO: 1), comprising an LCVR and an HCVR, wherein the LCVR is the polypeptide of SEQ ID NO: 9, and the HCVR is the polypeptide of SEQ ID NO: 11. The SEQ ID NOs are those disclosed in U.S. Pat. No. 8,980,582, and these sequences are explicitly incorporated herein by reference for possible use in the present invention and for possible inclusion in one or more claims herein.

In an embodiment, the antagonist comprises or consists of an antibody that binds to human BMP-6 (SEQ ID NO: 1), comprising a light chain (LC) and a heavy chain (HC), wherein the LC is the polypeptide of SEQ ID NO: 12, and the HC is the polypeptide of SEQ ID NO: 13 or SEQ ID NO: 14. In a further embodiment, the antagonist comprises or consists of an antibody that binds to human BMP-6 (SEQ ID NO: 1), comprising a LC and a HC, wherein the LC is the polypeptide of SEQ ID NO: 12, and the HC is the polypeptide of SEQ ID NO: 13. In another embodiment, the antagonist comprises or consists of an antibody that binds to human BMP-6 (SEQ ID NO: 1), comprising a LC and a HC, wherein the LC is the polypeptide of SEQ ID NO: 12, and the HC is the polypeptide of SEQ ID NO: 14. The SEQ ID NOs are those disclosed in U.S. Pat. No. 8,980,582, and these sequences are explicitly incorporated herein by reference for possible use in the present invention and for possible inclusion in one or more claims herein.

In an embodiment, the antagonist comprises or consists of an antibody that binds to human BMP-6 (SEQ ID NO: 1), comprising two light chains and two heavy chains, wherein each light chain is the polypeptide of SEQ ID NO: 12, and each heavy chain is the polypeptide of SEQ ID NO: 13. In an embodiment, the antagonist comprises or consists of an antibody that binds to human BMP-6 (SEQ ID NO: 1), comprising two light chains and two heavy chains, wherein each light chain is the polypeptide of SEQ ID NO: 12, and each heavy chain is the polypeptide of SEQ ID NO: 14. The SEQ ID NOs are those disclosed in U.S. Pat. No. 8,980,582, and these sequences are explicitly incorporated herein by reference for possible use in the present invention and for possible inclusion in one or more claims herein.

In an embodiment, the present invention provides a pharmaceutical composition comprising an anti-BMP6 antagonist (eg, an antibody, or antigen-binding fragment thereof) of the present invention, and an acceptable carrier, diluent, or excipient. More particularly, the compositions of the present invention further comprise one or more additional therapeutic agents, eg, an ESA and/or an anti-inflammatory agent. Suitable anti-inflammatory agents can be antibodies or antibody fragments, eg, an anti-TNF alpha antibody (eg, adalimumab, Humira®, infliximab, Remicade®, golimumab, Simponi®, or trap (eg, etanercept or Enbrel®); or anti-TNFR antibody or antibody fragment, or an anti-IL6R antibody (eg, sarilumab, tocilizumab or Actemra®).

In an example, the anti-BMP6 antagonist, antibody or fragment binds to BMP6 with a KD of less than about $1 \times 10^{-8}$ M, preferably, less than about $1 \times 10^{-9}$ M as determined by common methods known in the art, eg, by use of a surface plasmon resonance (SPR) biosensor at 37° C.

"Effective amount" means the amount of an antagonist (eg, antibody) or ESA of the present invention or pharmaceutical composition of the present invention that will elicit the biological or medical response or desired therapeutic effect on a subject, mammal or human that is being sought by the researcher, medical doctor, or other clinician. An effective amount may vary according to factors such as the disease state, age, sex, and weight of the individual, and the ability of the antibody and/or ESA to elicit a desired response in the individual. An effective amount is also one in which any toxic or detrimental effect is outweighed by the therapeutically beneficial effects.

The terms "treatment," "treat," "treating," and the like, are meant to include slowing or reversing the progression of a disorder, such as anaemia, moderate anaemia, severe anaemia or blood haemoglobin decrease. These terms also include alleviating, ameliorating, attenuating, eliminating, or reducing one or more symptoms of a disorder or condition (such as anaemia, moderate anaemia, severe anaemia or blood haemoglobin decrease), even if the disorder or condition is not actually completely eliminated. A subject or patient refers to a mammal, preferably a human with a disease, disorder or condition (eg, anaemia or at risk of anaemia) that would benefit from inhibition of BMP-6 activity. The term "preventing" is for example reducing the risk of a disease or condition, such as anaemia.

An ESA, anti-BMP6 antagonist antibody, or antigen-binding fragment thereof, of the present invention, or pharmaceutical composition comprising the same, may be administered by parenteral routes (eg, subcutaneous, intravenous, intraperitoneal, intramuscular, or transdermal). Administration may be to a subject alone or in combination with a pharmaceutically acceptable carrier and/or diluent in single or multiple doses. Pharmaceutical compositions, combinations or antagonists of the present invention can be prepared by methods well known in the art (e.g., *Remington: The Science and Practice of Pharmacy,* 19$^{th}$ ed. (1995), A. Gennaro et al., Mack Publishing Co.) and may comprise or be combined with one or more pharmaceutically acceptable carriers, diluents, or excipients.

In an example, the subject is suffering from moderate or severe anaemia prior to administration of the BMP6 antagonist and the moderate or severe anaemia is treated. In an embodiment, the subject is suffering from moderate anaemia prior to administration and after the treatment the subject has mild or no anaemia. In an embodiment, the subject is suffering from severe anaemia prior to administration and after the treatment the subject has mild, moderate or no anaemia. In an embodiment, after the treatment the subject has mild or no anaemia, and not moderate or severe anaemia. In another embodiment, after the treatment the subject does not have anaemia. In an embodiment, the subject has a blood haemoglobin level of less than 9.5 g/dL prior to administration and after the treatment the subject has a blood haemoglobin level of at least 10, 11, 12, 13 or 14 g/dL.

Anemia is generally considered when haemoglobin concentrations fall below 11 g/dL for pregnant women, 12 g/dL for non-pregnant women, and 13 g/dL for men.

The severity of anemia is categorized by the following haemoglobin concentration ranges:
  Mild anaemia is considered when haemoglobin is between 9.5-13.0 g/dL
  Moderate anaemia is considered when haemoglobin is between 8.0-9.5 g/dL
  Severe anaemia is considered for haemoglobin concentrations below 8.0 g/dL
  In an example, the level of haemoglobin is at or equivalent to a measurement at sea level.

In an embodiment, the subject is a human male, eg, an adult or infant. In an embodiment, the subject is a human female, eg, an adult or infant, eg, a non-pregnant female or pregnant female. I an example, the human is a dialysis patient. The infant may be a human that is >1 month old.

In an example, the method is a method of eliminating or reducing the need to administer iron or blood transfusion to a subject suffering from anaemia, Eg, for reducing the dose or dosing frequency of iron to the subject.

The invention may comprise simultaneously or sequentially administering the anti-BMP6 antagonist and ESA. In an example, antagonist and ESA are administered no more than 1 month, 4 weeks, 3 weeks, 2 weeks, 1 week, 10 days, 9 days, 8 days, 7 days, 6 days, 5 days, 4 days, 3 days, 2 days or 1 day apart. As exemplified herein, administration of the antagonist and ESA can be effective if no more than 7 days (eg, no more than one day) apart. In an example, the anti-BMP6 antagonist and ESA are administered to the subject no more than 10, 14, 21 or 28 days apart.

In an example, the ESA is administered 2, 3 or 4 times weekly. In an example, the ESA is administered 1, 2, 3 or 4 times monthly or in a 8 week period. In an example, the ESA (eg, epoetin alfa) is administered at a total dose of <3000, 2900, 2800, 2700, 2600, <2500, 2500, 2400, 2300, 2200, 2100, <2000, 2000, 1900, 1800, 1700, 1600, 1500, 1400, 1300, 1200, 1100 or 1000 units/kg per week. In another example, the ESA is administered 1, 2, 3 or 4 times monthly or in a 8 week period. In an example, the ESA (eg, darbepoetin alfa) is administered at a total dose of <15, <30, 12, 11, 10, 9, 8, 7, 6 or 5 mcg/kg per week.

In an example, the ESA and/or antagonist is administered to the subject intravenously or subcutaneously.

In an example, the anaemia is in a subject receiving or having received zidovudine treatment.

Optionally, any configuration of the invention is also for one or more of:—
(a) increasing or maintaining increased blood iron, eg, for treating or reducing the risk of anaemia;
(b) treating iron deficiency;
(c) treating or reducing the risk of Anaemia of Chronic Inflammation (ACI);
(d) treating or reducing the risk of Anaemia of Chronic Disease (ACD);
(e) treating or reducing the risk of anaemia associated with cancer, a kidney condition or GvHD;
(f) increasing blood or serum iron level;
(g) increasing reticulocyte count;
(h) increasing red blood cell count;
(i) increasing haemoglobin; and
(j) increasing haematocrit in the subject (eg, in a human).

In an embodiment, the invention is for regulating (eg, increasing) erythropoiesis in the subject.

In an embodiment, the subject is a human comprising BMP6 gene SNP rs111588693. This may be correlated with increased propensity for anaemia.

In an example, the anaemia is anaemia of chronic disease (ACD), such as anaemia of cancer, or anaemia of chronic kidney disease (CKD). Certain chronic diseases, such as cancer, kidney disease, and autoimmune disorders, can lead to ACD when overactive inflammatory cytokines cause dysregulation of iron homeostasis, reduction of erythropoiesis, and a decrease in the life span of red blood cells. Hepcidin has been identified as a key hormone involved in iron homeostasis; high levels of hepcidin have been associated with the iron restricted erythropoiesis seen in ACD. BMP-6 has been shown to increase hepcidin expression. In an example, the invention is for reducing or maintaining reduced hepcidin level in the subject.

Anaemia of CKD is anaemia that is an early and common complication in patients suffering with CKD. Anaemia of cancer is anaemia caused by haematological malignancies and some solid tumours; whereas, chemotherapy-induced (eg, immunotherapy-induced) anaemia is anaemia caused by the treatment of cancer patients with chemotherapeutic agents. Anaemia in CKD exacerbates diabetic neuropathy, cardiovascular disease, and retinopathy, among other conditions. Cancer-related anaemia is associated with an increased relative risk of death. Current treatment options for cancer-related anaemia are limited to blood transfusions, as erythropoiesis-stimulating agents are only indicated for chemotherapy-induced anaemia.

In an example, the subject is suffering from a chronic disease, such as cancer (eg, a haematological malignancy or a solid tumour), kidney disease, an autoimmune disorder or chemotherapy-induced anaemia. In an example, the subject (eg, human) is suffering from CKD and one or more of diabetic neuropathy, cardiovascular disease and retinopathy.

In an example, the anaemia is hepcidin related iron restricted anaemia. In an example, the anaemia is iron refractory iron deficiency anaemia (IRIDA). In an embodiment, the IRIDA is caused by a defect in the TMPRSS6 gene of the subject, eg, wherein IRIDA is caused by a TMPRSS6 gene mutation (eg, a SNP, such as rs855791; rs2543519; rs2235324; or rs1421312).

In an example, the method is a method of treating or preventing Sjogren's syndrome in addition to or instead of treating or preventing anaemia.

In an example, the invention is for increasing blood iron level, serum iron level, reticulocyte count, red blood cell count, haemoglobin, and/or haematocrit in the subject (eg, in a human).

In an embodiment, the present invention provides the use of an anti-BMP6 antagonist and an ESA for the manufacture of a medicament. In a further embodiment, the present invention provides the use of an anti-BMP6 antagonist and an ESA for the manufacture of a medicament for the treatment or prevention of anaemia, eg, moderate to severe anaemia. In another embodiment, the present invention provides the use of an anti-BMP6 antagonist and an ESA for the manufacture of a medicament for the treatment of anaemia of chronic disease. In another embodiment, the present invention provides the use of an anti-BMP6 antagonist and an ESA for the manufacture of a medicament for the treatment of anaemia of chronic kidney disease. In another embodiment, the present invention provides the use of an anti-BMP6 antagonist and an ESA for the manufacture of a medicament for the treatment of anaemia of cancer. In an embodiment, the present invention provides the use of an anti-BMP6 antagonist and an ESA for the manufacture of a medicament for the treatment of IRIDA. In a further embodiment, the present invention provides the use of an anti-BMP6 antagonist and an ESA for the manufacture of a medicament for the treatment of IRIDA, wherein IRIDA is caused by a TMPRSS6 gene mutation (eg, a SNP, such as rs855791; rs2543519; rs2235324; or rs1421312). In an embodiment, the present invention provides the use of an anti-BMP6 antagonist and an ESA for the manufacture of a medicament for the treatment of Sjogren's syndrome.

Clauses

Clauses of the invention are as follows, and these Clauses (and any un-numbered paragraphs) are combinable with any other configuration, example, feature or aspect of the invention as described herein; an antagonist (eg, anti-BMP6 antibody or fragment) or ESA of the invention can be provided for use in (or can be used in) an method in the following Clauses:—

1. An anti-Bone Morphogenetic Protein 6 (BMP6) antagonist for use in a method of treating or preventing anaemia in a subject, the method comprising administering said anti-BMP6 antagonist and an erythropoiesis stimulating agent (ESA) to the subject, wherein said anaemia is treated or prevented.

In an embodiment, the method is for treating anaemia in the subject, wherein said anaemia is treated.

In an example, the antagonist comprises or consists of an anti-BMP6 antibody or fragment, eg, a human, humanised or chimaeric antibody. In an alternative to an antibody or fragment, a different BMP6 antagonist is contemplated by the invention, eg, an anti-BMP6 trap or a HJV-Fc.

2. An antagonist according to Clause 1, wherein the antagonist comprises or consists of an anti-BMP6 antibody or fragment, the method comprising
   (a) on an initial day ($D_0$) administering to the subject the anti-BMP6 antibody or fragment; and
   (b) in a period of at least 3 consecutive weeks, said period starting on $D_0$, administering a plurality of doses of an ESA wherein blood Hb concentration in said subject is elevated from a baseline concentration on $D_0$ for the entire duration of said period,
   such that:—
   (i) for the entire duration of said period Hb concentration is no lower than 100% of baseline Hb concentration; and during said period Hb concentration reaches at least 120% of baseline; and/or
   (ii) for the entire duration of said period Hb concentration is increased over baseline by at least 1 g/dl.

In any Clause herein, in an example for the entire duration of said period Hb concentration is increased over baseline by at least 1 g/dl, eg, by at least 1.5, 2 or 2.5 g/dl. In an example, Hb concentration is no more than 11. 11.5 or 12 g/dl in the subject, eg, an adult male or female human.

Hb concentrations and MCH (see below) may be determined using one or more blood samples obtained from the subject. For example, as determined using a blood sample taken at the end of each week of said period (and the baseline determined using a sample taken at $D_0$).

3. A combination of an amount of anti-BMP6 antibody or fragment and an amount of an ESA (eg, comprising multiple doses of said ESA) for use in a method of treating anaemia, wherein the antibody, fragment and method are according to Clause 2.

4. The combination of Clause 3, wherein the method comprises obtaining a single dose from said amount of antibody or fragment, wherein the single dose is administered to the subject on $D_0$, and obtaining a plurality of doses of said ESA, wherein at least one dose is administered weekly from $D_0$.

In any Clause herein, in an example the first dose of ESA is administered on $D_0$ 5. The combination of Clause 3 or 4, wherein the antibody or fragment is comprised by a pharmaceutical composition, wherein the antibody or fragment is mixed with a dose of the ESA for administration to said subject on $D_0$.

6. A medical kit comprising the combination of any one of Clauses 3 to 5, a first sterile container comprising said amount of antibody or fragment, and a second sterile container comprising said amount of ESA, and optionally instructions for carrying out said method.

7. An antagonist according to Clause 1, wherein the antagonist comprises or consists of an erythropoietin stimulating agent (ESA) (eg, comprised by multiple doses of said ESA), the method comprising
   (a) on an initial day ($D_0$) administering to the subject an anti-BMP6 antibody or fragment; and
   (b) in a period of at least 3 consecutive weeks, said period starting on $D_0$, administering a plurality of doses of said ESA wherein blood haemoglobin (Hb) concentration in said subject is elevated from a baseline concentration on $D_0$ for the entire duration of said period,
   such:—
   (i) for the entire duration of said period Hb concentration is no lower than 100% of baseline Hb concentration; and during said period Hb concentration reaches at least 120% of baseline; and/or
   (ii) for the entire duration of said period Hb concentration is increased over baseline by at least 1 g/dl.

8. The antagonist, combination or kit of any one of Clauses 2 to 7, wherein
   (iii) the Hb concentration on the last day of said consecutive week period is at least 120% of the Hb concentration on the $7^{th}$ day immediately preceding said last day.

9. The antagonist, combination or kit of any one of Clauses 2 to 8, wherein ESA is administered to the subject within 24 hours of administration of the anti-BMP6 antibody or fragment.

10. The antagonist, combination or kit of any one of Clauses 2 to 9, wherein said consecutive week period consists of a period of 3 or 4 consecutive weeks.

11. The antagonist, combination or kit of any one of Clauses 2 to 10 (eg, Clause 10), wherein during said period Hb concentration reaches an increase in the range from 1 to 8 g/dl over baseline.

In any Clause herein, in an example during said period Hb concentration reaches an increase in the range from 1 to 3, 2.5, 2, 1.5 or 1.25 g/dl over baseline. For example the Hb concentration reaches an increase from 1 to 2 g/dl.

12. The antagonist, combination or kit of any one of Clauses 2 to 11, wherein the period consists of 3 or 4 consecutive weeks and at the end of said period Hb concentration reaches at least 150% of baseline.

13. The antagonist, combination or kit of any one of Clauses 2 to 12, wherein the period consists of 3 or 4 consecutive weeks and
    (a) for the entire duration of said period Hb concentration is no lower than 110% of baseline Hb concentration; and during said period Hb concentration reaches at least 150% of baseline; and/or
    (b) for the entire duration of said period Hb concentration is increased over baseline by at least 1 g/dl and during said period Hb concentration reaches an increase in the range from 1 to 8 g/dl over baseline. For example the Hb concentration reaches an increase from 1 to 2 g/dl.

14. The antagonist, combination or kit of any one of Clauses 2 to 13, wherein in said period the antibody or fragment is administered on $D_0$.

15. The antagonist, combination or kit of Clause 14, wherein the antibody or fragment is administered as a single dose on $D_0$ to the subject.

In any Clause herein, in an example the antibody or fragment is administered as a single dose on $D_0$ to the subject, wherein the single dose is administered in one or a plurality of aliquots to the subject.

16. The antagonist, combination or kit of any one of Clauses 2 to 15, wherein an initial ESA dose is administered on $D_0$ or no more than 2 days thereafter.

17. The antagonist, combination or kit of any one of Clauses 2 to 16, wherein an ESA dose is administered on the 4-$9^{th}$ (eg, on the $7^{th}$) day immediately after $D_0$.

18. The antagonist, combination or kit of any one of Clauses 2 to 17, wherein a ESA dose is administered on the 12-16$^{th}$ (eg, on the 14$^{th}$) day immediately after $D_0$.
19. The antagonist, combination or kit of any one of Clauses 2 to 18, wherein a ESA dose is administered on the 19-23$^{rd}$ (eg, on the 21$^{st}$) day immediately after $D_0$.

In any Clause herein, in an example an ESA dose is administered in each of (i) the 4-9$^{th}$ (eg, on the 7$^{th}$) day, (ii) the 12-16$^{th}$ (eg, on the 14$^{th}$) day and (iii) the 19-23$^{rd}$ (eg, on the 21$^{st}$) day immediately after $D_0$.

20. The antagonist, combination or kit of any one of Clauses 2 to 19, wherein an equivalent of 4 ESA doses is administered during said period.

By "equivalent" here, it is intended that a plurality of aliquots of the ESA can be administered (eg, on the same day or sequentially), wherein the aliquots amount to a total dose of the ESA. In an example, the ESA is darbepoetin alfa or Aranesp® and a dose is in the range from 15 to 100 mcg (micrograms); or from 30 to 100 mcg. In an example, the ESA is epoetin alfa and a dose is in the range from 3000 to 30000 units (ie, units refers to International Units, also known as IU, UI, IE, ME, NE in various languages).

Generally herein, a dose (eg, of antibody, fragment or ESA) can be administered in one aliquot or a plurality of aliquots (eg, on the same day, simultaneously, within a 30, 1 or 24 hour window).

21. The antagonist, combination or kit of any one of Clauses 2 to 20, wherein ESA is administered to the subject during each of the first and second weeks after the initial ESA dose.
22. The antagonist, combination or kit of any one of Clauses 2 to 21, wherein ESA is administered to the subject during each of the first, second and third weeks after the initial ESA dose.
23. The antagonist, combination or kit of Clause 21 or 22, wherein ESA is administered as a single dose at the end of each said week, optionally wherein said period consists of 3 or 4 weeks starting at $D_0$.

In an example of any of the Clauses, said period consists of 4 weeks starting at $D_0$ and anaemia is treated in the 4$^{th}$ week.

24. The antagonist, combination or kit of any one of Clauses 2 to 23, wherein no more than 4 doses of ESA are administered to the subject during said period and optionally a single dose of said antibody or fragment.
25. The antagonist, combination or kit of any one of Clauses 2 to 24, wherein over said period (wherein the period is a 4 consecutive week period), the total dose of the antibody and total dose of ESA are administered to said subject in a ratio of X:Y, wherein X is from 10 to $2\times10^6$ and Y=4.

In an example, a total weekly dose of ESA (eg, wherein the subject is a human) is from 10 or 15 to 80, 100, 200 or 300 mcg (micrograms). For example, the total weekly dose is from 10 to 80; from 15 to 80; or from 30 to 80 mcg. For example, the ESA comprises or consists of darbepoetin alfa, epoetin alfa or any other ESA disclosed herein. In an example, each dose of ESA (or a weekly dose) is administered to the subject in the range from 1.5 to 2 mcg/kg ESA.

In certain configurations, the method relates to reducing or sparing the administration of ESA. In this instance, for example, a total weekly dose of ESA (eg, wherein the subject is a human) is from 1 to 20 mcg, eg, from 1 up to 15 mcg. In an example where there is ESA sparing or reduction, each dose of ESA (or a weekly dose) is administered to the subject in the range from 0.01 or 0.1 to 0.3 or 1 mcg/kg ESA, eg, from 0.01 to 0.3; or from 0.1 to 0.3; or from 0.01 to 1; or from 0.1 to 1 mcg/kg.

26. The antagonist, combination or kit of any one of Clauses 2 to 25, wherein Hb concentration at the end of said period (eg, a 3 or 4 consecutive week period) is at least 130% of Hb concentration in a control anaemia patient of the same species that has received administration of the anti-BMP6 antibody or fragment in the same dosing regimen as said subject except the patient has not received administration of an ESA during said period.
27. The antagonist, combination or kit of Clause 26, wherein said Hb concentration at the end of said period is significantly higher than in said control at the end of said period, as determined by a p-value of $p<0.0001$.
28. The antagonist, combination or kit of any one of Clauses 2 to 27, wherein mean corpuscular haemoglobin (MCH) at the end of said period is at least 109% of MCH in a control anaemia patient of the same species that has received administration of the anti-BMP6 antibody or fragment in the same dosing regimen as said subject except the patient has not received administration of an ESA during said period.

The mean corpuscular haemoglobin (MCH) is the average mass of haemoglobin per red blood cell in a sample of blood.

29. The antagonist, combination or kit of any one of Clauses 2 to 28, wherein Hb concentration at the end of said period (eg, a 3 or 4 consecutive week period) is at least 120% of Hb concentration in a control anaemia patient of the same species that has received administration of said ESA in the same dosing regimen as said subject except the patient has not received administration of an anti-BMP6 antibody or fragment during said period. Optionally, the control patient has received a control IgG4 antibody that does not specifically bind BMP6 (eg, wherein the BMP6 antibody and the control antibody are administered to the subject and control patient respectively in the same dose). Optionally, X is from 10 to $2\times10^5$, $2\times10^4$ or $2\times10^3$.
30. The antagonist, combination or kit of Clause 29, wherein said Hb concentration at the end of said period is significantly higher than in said control at the end of said period, as determined by a p-value of $p<0.0001$.
31. The antagonist, combination or kit of any one of Clauses 2 to 30, wherein mean corpuscular haemoglobin (MCH) at the end of said period (eg, a 3 or 4 consecutive week period) is at least 119% of MCH in a control anaemia patient of the same species that has received administration of said ESA in the same dosing regimen as said subject except the patient has not received administration of an anti-BMP6 antibody or fragment during said period.
32. The antagonist, combination or kit of Clause 31, wherein said MCH at the end of said period is significantly higher than in said control at the end of said period, as determined by a p-value of $p<0.0001$.
33. The antagonist, combination or kit of any one of Clauses 2 to 32, wherein said subject at $D_0$ suffers from anaemia of chronic disease (ACD) and optionally wherein the anaemia is associated with chronic inflammation (eg, the subject suffers from arthritis) or a bacterial infection (eg, *Streptococcus* infection), or wherein the subject is a chronic kidney disease (CKD) patient.
34. The antagonist, combination or kit of any one of Clauses 2 to 33, wherein the anaemia in said subject at the end of said period is less severe than on $D_0$.
35. The antagonist of Clause 1, wherein the antagonist comprises or consists of an anti-BMP6 antibody or fragment.

36. The antagonist, combination or kit of any one of Clauses 2 to 34, wherein the antibody or fragment competes with a reference antibody for binding BMP6, wherein the reference antibody is mAb507 (R&D Systems) or an antibody comprising
   a. Heavy chains each comprising or consisting of the amino acid sequence of SEQ ID NO: 1 or 2, and light chains each comprising or consisting of the amino acid sequence of SEQ ID NO: 3; or
   b. Heavy chains each comprising or consisting of the amino acid sequence of SEQ ID NO: 4 and light chains each comprising or consisting of the amino acid sequence of SEQ ID NO: 5.

Competition herein can, for example, be determined by SPR (eg, at 37 degrees C. at pH7.6 and optionally as a Fab); by ELISA; by fluorescence activated cell sorting (FACS); or in a homogenous time resolved fluorescence (HTRF) assay. SPR may be carried out using Biacore™, Proteon™ or another standard SPR technique. In one embodiment, competition is determined by ForteBio Octet® Bio-Layer Interferometry (BLI) such techniques being readily apparent to the skilled person.

In an alternative, the reference antibody is any anti-BMP6 antibody disclosed in WO2016098079 (the sequences and disclosure relating to such antibodies being incorporated herein for potential use in the present invention).

37. The antagonist, combination or kit of any one of Clauses 2 to 36, wherein the antibody or fragment competes with said reference antibody for binding to SEQ ID NO: 6. Said SEQ ID NO: 6 can be used as a peptide per se, part of a larger peptide or part of a BMP6 protein (eg, a wild type human BMP6 or recombinantly produced BMP6).

Additionally or alternatively, the antibody or fragment competes with said reference antibody for binding to a further sequence selected from the group consisting of SEQ ID NOs: 7-19. Said further sequence can be used as a peptide per se, part of a larger peptide (eg, comprising SEQ ID NO: 6) or part of a BMP6 protein (eg, a wild type human BMP6 or recombinantly produced BMP6, eg, comprising SEQ ID NO: 6). For example, the antibody or fragment competes with said reference antibody for binding to SEQ ID NO: 7. For example, the antibody or fragment competes with said reference antibody for binding to SEQ ID NO: 8. For example, the antibody or fragment competes with said reference antibody for binding to SEQ ID NO: 9. For example, the antibody or fragment competes with said reference antibody for binding to SEQ ID NO: 10. For example, the antibody or fragment competes with said reference antibody for binding to SEQ ID NO: 11. For example, the antibody or fragment competes with said reference antibody for binding to SEQ ID NO: 12. For example, the antibody or fragment competes with said reference antibody for binding to SEQ ID NO: 13. For example, the antibody or fragment competes with said reference antibody for binding to SEQ ID NO: 14. For example, the antibody or fragment competes with said reference antibody for binding to SEQ ID NO: 15. For example, the antibody or fragment competes with said reference antibody for binding to SEQ ID NO: 16. For example, the antibody or fragment competes with said reference antibody for binding to SEQ ID NO: 17. For example, the antibody or fragment competes with said reference antibody for binding to SEQ ID NO: 18. For example, the antibody or fragment competes with said reference antibody for binding to SEQ ID NO: 19.

38. The antagonist, combination or kit of any one of Clauses 2 to 37, wherein the antibody or fragment competitively inhibits the binding of soluble haemojuvelin (HJV) to BMP6.

39. The antagonist, combination or kit of any one of Clauses 1 to 38, wherein the antibody or fragment does not competitively inhibit the binding of soluble haemojuvelin (HJV) to BMP6 (eg, as determined by SPR, HTRF or ELISA).

40. The antagonist, combination or kit of any one of Clauses 2 to 39, wherein the antibody comprises VH domains encoded by a VDJ region sequence, wherein the VDJ is derived from the recombination of a VH gene segment, D gene segment and JH gene segment, wherein the VH is a human germline (i) VH1-3, (ii) VH2-5 or (iii) VH3-15 gene segment.

41. The antagonist, combination or kit of any one of Clauses 2 to 40, wherein the antibody comprises VL domains encoded by a VJ region sequence, wherein the VJ is derived from the recombination of a VL gene segment and JL gene segment, wherein the VL is a human germline (iv) Vκ3-20, (v) Vλ3-1, (vi) Vκ1-17 or (vii) Vλ1-40.

42. The antagonist, combination or kit of any one of Clauses 2 to 41, wherein the antibody or fragment binds to BMP6 with a stronger affinity (lower KD determined by SPR) than binding to BMP7; and optionally binds to BMP6 with a stronger affinity than to BMP5.

Optionally the antibody or fragment binds to BMP6 with a stronger affinity than to each of BMP2, 4, 5 and 9.

43. The antagonist, combination or kit of any one of Clauses 2 to 42, wherein the antibody or fragment binds to a human BMP6 sequence comprising SEQ ID NO: 6.

44. The antagonist, combination or kit of any one of Clauses 2 to 43, wherein the antibody has an affinity (KD) for binding BMP6 of from 1 pM to 5 nM, optionally wherein binding is determined by SPR using a Fab of said antibody at 37° C. at pH 7.6.

In an example, the antibody (eg, as a Fab) or fragment has an affinity (KD) for binding BMP6 of
   (a) from 2, 3, 4, 5 or 10 pM to 3, 4 or 5 nM;
   (b) from 1-10 pM to 5 nM;
   (c) from 10 pM to 3, 4 or 5 nM;
   (d) from 50 or 80 pM to 200 nM;
   (e) from 50 or 80 pM to 150 nM; or
   (f) from 50 or 80 pM to 100 nM.

In an example, the KD is (or is about) 5-15 pM (eg, 10 pM). In an example, the KD is (or is about) 2-5 nM (eg, 3 nM). In an example, the KD is (or is about) 100-400 pM (eg, 140 or 390 pM).

45. The antagonist, combination or kit of any one of Clauses 2 to 44 (eg, Clause 44), wherein the antibody has off-rate ($K_{off}$) for binding BMP6 of from $1\times10^{-5}$ to $1\times10^{-3}$ $S^{-1}$, optionally wherein binding is determined by SPR using a Fab of said antibody at 37° C. at pH 7.6.

In an example, the antibody (eg, as a Fab) or fragment has an off-rate ($K_{off}$) for binding BMP6 of
   (a) from $1\times10^{-5}$ to $5\times10^{-4}$ $S^{-1}$;
   (b) from $1\times10^{-5}$ to $6\times10^{-4}$ $S^{-1}$;
   (c) from $1\times10^{-5}$ to $7\times10^{-4}$ $S^{-1}$;
   (d) from $1\times10^{-5}$ to $8\times10^{-4}$ $S^{-1}$;
   (e) from $2\times10^{-5}$ to $1\times10^{-3}$ $S^{-1}$;
   (f) from $2\times10^{-5}$ to $5\times10^{-4}$ $S^{-1}$;
   (g) from $2\times10^{-5}$ to $6\times10^{-4}$ $S^{-1}$;
   (h) from $2\times10^{-5}$ to $7\times10^{-4}$ $S^{-1}$; or
   (i) from $2\times10^{-5}$ to $8\times10^{-4}$ $S^{-1}$.

In an example, the $K_{off}$ is (or is about) $5\times10^{-4}$ $S^{-1}$ (eg, when the KD is (or is about) from 2 nM to 400 pM; when the KD is (or is about) 2-5 nM (eg, 3 nM); or when the KD is (or is about) 100-400 pM (eg, 140 or 390 pM)). In an example, the $K_{off}$ is (or is about) $3\times10^{-5}$ $S^{-1}$ (eg, when the KD is (or is about) from 5-15 pM (eg, 10 pM)).

46. The antagonist, combination or kit of any one of Clauses 2 to 45 (eg, Clause 44 and/or 45), wherein the antibody has on-rate ($K_{on}$) for binding BMP6 of from $1\times10^5$ to $1\times10^7$ $M^{-1}S^{-1}$, optionally wherein binding is determined by SPR using a Fab of said antibody at 37° C. at pH 7.6.

In an example, the antibody (eg, as a Fab) or fragment has an on-rate ($K_{on}$) for binding BMP6 of
   (a) from $1\times10^5$ to $1\times10^6 M^{-1}S^{-1}$;
   (b) from $1\times10^5$ to $2\times10^6$ $M^{-1}S^{-1}$;
   (c) from $1\times10^5$ to $3\times10^6$ $M^{-1}S^{-1}$;
   (d) from $1\times10^5$ to $4\times10^6$ $M^{-1}S^{-1}$;
   (e) from $1\times10^5$ to $5\times10^6$ $M^{-1}S^{-1}$;
   (f) from $2\times10^5$ to $5\times10^6$ $M^{-1}S^{-1}$;
   (g) from $3\times10^5$ to $5\times10^6$ $M^{-1}S^{-1}$;
   (h) from $4\times10^5$ to $5\times10^6$ $M^{-1}S^{-1}$;
   (i) from $5\times10^5$ to $5\times10^6$ $M^{-1}S^{-1}$; or
   (j) from $6\times10^5$ to $5\times10^6$ $M^{-1}S^{-1}$.

In an example, the $K_{on}$ is (or is about) 1 or $2\times10^{-5}$ $M^{-1}S^{-1}$ (eg, when the KD is 2-5 nM (eg, 3 nM)). In an example, the $K_{on}$ is (or is about) 1-4, 1, 2, 3 or $4\times10^{-6}$ $M^{-1}S^{-1}$ (eg, when the KD is (or is about) from 5-400 pM (eg, 140 or 390 pM) or 5-15 pM (eg, 10 pM)).

47. The antagonist, combination or kit of any one of Clauses 2 to 46, wherein
   (a) the period consists of 3 or 4 consecutive weeks and
      (i) for the entire duration of said period Hb concentration is no lower than 110% of baseline Hb concentration; and during said period Hb concentration reaches at least 120% of baseline; and/or
      (ii) for the entire duration of said period Hb concentration is increased over baseline by at least 1 g/dl and during said period Hb concentration reaches an increase in the range from 1 to 8 g/dl over baseline;
   (b) wherein a dose of ESA is administered at least twice during the first two or three weeks of said period;
   (c) wherein the antibody or fragment binds to BMP6 with a stronger affinity (lower KD determined by SPR) than binding to BMP7; and optionally binds to BMP6 with a stronger affinity than to BMP5 (and optionally binds to BMP6 with a stronger affinity than to each of BMP2, 4, 5 and 9); and
   (d) wherein the antibody or fragment competes with a reference antibody for binding BMP6, wherein the reference antibody is mAb507 (R&D Systems) or an antibody comprising
      I. Heavy chains each comprising or consisting of the amino acid sequence of SEQ ID NO: 1 or 2, and light chains each comprising or consisting of the amino acid sequence of SEQ ID NO: 3; or
      II. Heavy chains each comprising or consisting of the amino acid sequence of SEQ ID NO: 4 and light chains each comprising or consisting of the amino acid sequence of SEQ ID NO: 5.

Optionally, in part I the heavy chains consist of the amino acid sequence of SEQ ID NO: 1 and the light chains consist of the amino acid sequence of SEQ ID NO: 3. Optionally, in part I the heavy chains consist of the amino acid sequence of SEQ ID NO: 2 and the light chains consist of the amino acid sequence of SEQ ID NO: 3. Optionally, in part II the heavy chains consist of the amino acid sequence of SEQ ID NO: 4 and the light chains consist of the amino acid sequence of SEQ ID NO: 5.

In an example (as per the antibody used in Example 2 below), in part (d) the anti-BMP6 antibody of the invention is an antibody that competes with a reference antibody of part I or part II in an HTRF assay. For example, wherein in the HTRF assay the antibody of the invention is a labelled antibody that is pre-incubated with human BMP6 and subsequently combined with unlabelled reference antibody (according to part I or II), wherein competition between the antibodies is detected by the assay. In an example, the assay uses AlexaFluor™ 647 labelled antibody of the invention. In an alternative, the human BMP6 is labelled (eg, with AlexaFluor™ 647, the test antibody is labelled with biotin for binding to Eu3+cryptate-streptavidin, and the reference antibody is unlabelled).

Optionally, the anti-BMP6 antibody of the invention (test antibody) competes in an HTRF assay with the reference antibody for binding human BMP6 (or binds the same epitope of human BMP6 as the reference antibody), wherein the assay uses a directly or indirectly labelled test antibody directly or indirectly labelled with a donor (such as for example Eu3+cryptate) or an acceptor fluorophore (such as for example AlexaFluor™ 647) and a target BMP6 labelled with either a donor or acceptor fluorophore to enable energy transfer between donor and acceptor, whereby a fluorescence signal is produced and detected. In an example, where AlexaFluor™ 647 labelling is used, competition is detected by a reduction in fluorescence signal at 665 nM of at least 20% when the test antibody is in the presence of the reference antibody versus signal without the reference antibody. Optionally, the reduction in signal at 665 nM is at least 20, 30, 40, 50, 60, 70, 80 or 90%.

Optionally, the anti-BMP6 antibody (test antibody) is one that competes in a HTRF assay with a reference antibody for binding human BMP6 (or binds the same epitope of human BMP6 as the reference antibody), wherein the reference antibody comprises heavy chains each comprising the amino acid sequence of SEQ ID NO: 1 or 2, and light chains each comprising the amino acid sequence of SEQ ID NO: 3, wherein the assay uses the test antibody directly or indirectly labelled with a donor label (such as for example Eu3+cryptate) or an acceptor fluorophore label (such as for example AlexaFluor™ 647) and a human BMP6 labelled with either an acceptor fluorophore or donor respectively to enable energy transfer between donor and acceptor, wherein said competition between the antibodies is detected by a reduction in fluorescence signal of at least 20% when the test antibody is in the presence of the reference antibody versus signal without the reference antibody. For example, the test antibody is directly or indirectly labelled with AlexaFluor™ 647 and competition is detected by a reduction in fluorescence signal at 665 nM of at least 20% when the test antibody is in the presence of the reference antibody versus signal without the reference antibody. Optionally, the reduction in signal at 665 nM is at least 20, 30, 40, 50, 60, 70, 80 or 90%.

Optionally, the anti-BMP6 antibody (test antibody) also competes in an HTRF assay with a reference antibody for binding human BMP6 (or binds the same epitope of human BMP6 as the reference antibody), wherein the reference antibody comprises heavy chains each comprising the amino acid sequence of SEQ ID NO: 4, and light chains each comprising the amino acid sequence of SEQ ID NO: 5, wherein the assay for example uses the test antibody directly or indirectly labelled with a donor label (such as for example Eu3+cryptate) or an acceptor fluorophore label (such as for example AlexaFluor™ 647) and a human BMP6 labelled with either an acceptor fluorophore or donor respectively to enable energy transfer between donor and acceptor, wherein said competition between the antibodies is detected by a reduction in fluorescence signal of at least 20% when the test antibody is in the presence of the reference antibody versus signal without the reference antibody. For example, the test antibody is directly or indirectly labelled with AlexaFluor™ 647 and competition is detected by a reduction in fluorescence signal at 665 nM of at least 20% when the test antibody is in the presence of the reference antibody versus signal without the reference antibody. Optionally, the reduction in signal at 665 nM is at least 20, 30, 40, 50, 60, 70, 80 or 90%.

For example in part (b) a dose of ESA is administered 2, 3 or 4 times during the first 3 weeks of said period, or during said period.

In an alternative, the reference antibody is any anti-BMP6 antibody disclosed in WO2016098079 (the sequences and disclosure relating to such antibodies being incorporated herein for potential use in the present invention).

48. The antagonist, combination or kit of any one of Clauses 1 to 47 for
    a. treating ACD in the subject;
    b. treating or preventing moderate or severe anaemia in the subject;
    c. treating or preventing anaemia in the subject, wherein the subject suffers from an inflammatory disease or condition;
    d. eliminating or reducing the need to administer iron or blood transfusion to the subject;
    e. treating or preventing anaemia in the subject, wherein the subject suffers from a microbial infection; or
    f. reducing administration of ESA to the subject.
49. A method of treating anaemia in a subject, the method comprising
    (a) on an initial day ($D_0$) administering to the subject an anti-BMP6 antibody or fragment; and
    (b) in a period of at least 3 consecutive weeks, said period starting on $D_0$, administering a plurality of doses of an erythropoietin stimulating agent (ESA) wherein blood haemoglobin (Hb) concentration in said subject is elevated from a baseline concentration on $D_0$ for the entire duration of said period,
    such that for the entire duration of said period:—
    (i) Hb concentration is no lower than 100% of baseline Hb concentration; and during said period Hb concentration reaches at least 120% of baseline; and/or
    (ii) Hb concentration is increased over baseline by at least 1 g/dl.
50. The method of Clause 49, wherein the method, antibody fragment or ESA is as recited in any one of Clauses 2 to 48.
51. The antagonist, combination, kit or method of any preceding Clause, wherein the anaemia is moderate or severe anaemia.
52. An anti-Bone Morphogenetic Protein 6 (BMP6) antagonist for use in a method of maintaining a blood haemoglobin (Hb) level of at least 10 g/dL in a subject, the method comprising administering an anti-BMP6 antagonist and an erythropoiesis stimulating agent (ESA) to the subject.
53. An anti-Bone Morphogenetic Protein 6 (BMP6) antagonist for use in a method of preventing the blood haemoglobin level of a subject from decreasing to less than 10 g/dL, the method comprising administering an anti-BMP6 antagonist and an erythropoiesis stimulating agent (ESA) to the subject.
54. An anti-Bone Morphogenetic Protein 6 (BMP6) antagonist for use in a method of raising blood haemoglobin to a level of at least 10 g/dL in a subject suffering from anaemia, the method comprising administering an anti-BMP6 antagonist and an erythropoiesis stimulating agent (ESA) to the subject, wherein said anaemia is treated.
55. An anti-Bone Morphogenetic Protein 6 (BMP6) antagonist for use in a method of treating or preventing anaemia in a subject suffering from an inflammatory disease or condition, the method comprising administering an anti-BMP6 antagonist and an erythropoiesis stimulating agent (ESA) to the subject, wherein said anaemia is treated or prevented.
56. An anti-Bone Morphogenetic Protein 6 (BMP6) antagonist for use in a method of eliminating or reducing the need to administer iron or blood transfusion to a subject suffering from anaemia, the method comprising administering an anti-BMP6 antagonist and an erythropoiesis stimulating agent (ESA) to the subject, wherein said need is eliminated or reduced.
57. An anti-Bone Morphogenetic Protein 6 (BMP6) antagonist for use in a method of treating or preventing anaemia in a subject suffering from a microbial infection, the method comprising administering an anti-BMP6 antagonist and an erythropoiesis stimulating agent (ESA) to the subject.
58. An anti-Bone Morphogenetic Protein 6 (BMP6) antagonist for use in a method of reducing administration of an erythropoiesis stimulating agent (ESA) to a subject suffering from anaemia for treating anaemia, the method comprising administering an anti-BMP6 antagonist and said ESA, wherein anaemia is treated in the subject.
59. An anti-Bone Morphogenetic Protein 6 (BMP6) antagonist for use in a method of treating or reducing the risk of anaemia in a subject suffering from or at risk of anaemia, the method comprising administering an anti-BMP6 antagonist and a low dose of an erythropoiesis stimulating agent (ESA) to the subject, wherein anaemia is treated or the risk of anaemia is reduced in the subject.
60. The antagonist of any one of Clauses 52 to 59, wherein the antagonist is according to any one of Clauses 1 to 1, 2, 7 to 48 and 51.
61. The antagonist of any one of Clauses 52 to 59, wherein the antagonist is according to any other of Clauses 52 to 59.
62. The antagonist, combination, kit or method of any preceding Clause, wherein the ESA is
    a. Epoetin alfa and is administered at a weekly dose of less than 1000, 1500, 2500, 5000, 11000, 18000, 34000 or 90000 units, optionally wherein the subject has previously received a weekly epoetin alfa treatment of <1500, 1500 to 2499, 2500 to 4999, 5000 to 10999, 11000 to 17999, 18000 to 33999, 34000 to 89999 or ≥90000 units respectively;
    b. darbepoetin alfa or Aranesp® and is administered at a weekly dose of less than 6.25, 10, 12.5, 20, 25, 40, 60, 100 or 200 mcg, optionally wherein the subject has previously received a weekly darbepoetin alfa or Aranesp® treatment of 6.25, 10, 12.5, 20, 25, 40, 60, 100 or 200 mcg respectively; or
    c. darbepoetin alfa or Aranesp® and is administered at a weekly dose of less than 6.25, 10, 20, 40, 60, 100 or 200 mcg, optionally wherein the subject has previously received a weekly Epoetin alfa treatment of 1500 to 2499, 2500 to 4999, 5000 to 10999, 11000 to 17999, 18000 to 33999, 34000 to 89999 or ≥90,000 units respectively.

63. The antagonist, combination, kit or method of any preceding Clause, wherein the anti-BMP6 antagonist is an antibody and each dose is administered at a total of no more than 30 mg/kg.
64. An anti-BMP6 antagonist and/or an ESA for use in a therapeutic regimen method for treating or preventing anaemia in a subject suffering from or at risk of anaemia, the regimen comprising simultaneously or sequentially administering an anti-BMP6 antagonist and an ESA to the subject, wherein
    a. On day zero the antagonist is administered to the subject; and no later than day 7 (eg, on day 1) the ESA is administered to the subject; or
    b. On day zero the ESA is administered to the subject; and no later than day 7 (eg, on day 1) the antagonist is administered to the subject; or
    c. On day zero the antagonist and the ESA are simultaneously administered to the subject; or
    d. On day zero the subject has already received the ESA and on day zero the antagonist is administered to the subject; or
    e. On day zero the subject has already received the antagonist and on day zero the ESA is administered to the subject;
    whereby at day 14 or later the blood haemoglobin level is at least 10 g/dL in the subject,
    wherein said anaemia is treated or prevented.
65. The antagonist and/or ESA according to Clause 64, which is further according to any one of Clauses 1 to 1, 2, 7 to 48 and 51.
66. The antagonist and/or ESA according to Clause 64 or 65, wherein the anti-BMP6 antagonist and ESA are administered to the subject no more than 7 days apart.
67. The antagonist and/or ESA according to Clause 64, 65 or 66, wherein the regimen maintains blood Hb level in the subject at more than 10 g/dL in the subject.
68. The antagonist and/or ESA according to any one of Clauses 64 to 67, wherein the method maintains or raises blood haemoglobin level to at least 10 g/dL in the subject at least 13 or 14 days after the subject has received the anti-BMP6 antagonist and ESA.
69. The antagonist and/or ESA according to Clause 67 or 68, wherein the anti-BMP6 antagonist and ESA are administered to the subject no more than 1 day apart.
70. The antagonist and/or ESA according to any one of Clauses 64 to 69, wherein the anti-BMP6 antagonist and ESA are administered to the subject simultaneously.
71. The antagonist and/or ESA according to any one of Clauses 64 to 70, wherein the blood haemoglobin level of the subject is prevented from decreasing to less than 10 g/dL (eg, at day 14).
72. The antagonist and/or ESA according to any one of Clauses 64 to 71, wherein the blood haemoglobin of the subject is raised to a level of at least 10 g/dL (eg, at day 14).
73. The antagonist and/or ESA according to any one of Clauses 64 to 72, wherein moderate or severe anaemia is prevented in the subject (eg, at day 14).
74. The antagonist, combination, kit, ESA or method of any preceding Clause, wherein the subject is suffering from
    a. an inflammatory disease or condition; or
    b. an infection;
    c. kidney disease;
    d. HIV or undergoing HIV treatment; or
    e. cancer; and
    anaemia is treated or prevented in the subject.
75. The antagonist, combination, kit, ESA or method of any preceding Clause, wherein the subject is a mammal.
76. The antagonist, combination, kit, ESA or method of any preceding Clause, in combination with an anti-inflammatory agent, or wherein an anti-inflammatory agent is administered to the subject.
77. The antagonist, combination, kit, ESA or method of any preceding Clause, wherein the ESA is an erythropoietin.

In an example, the subject is suffering from chronic kidney disease (CKD). Reference is made to "KDIGO Clinical Practice Guideline for Anemia in Chronic Kidney Disease", Kidney International Supplements (2012) 2, 279; doi:10.1038/kisup.2012.37. This discusses stages of chronic kidney disease (stages 1-5), diagnosis, CKD nomenclature, Hb levels and ranges in humans of various ages and ESA hyporesponsiveness. This reference discloses:—

Diagnosis of anemia
  Diagnose anemia in adults and children>15 years with CKD when the Hb concentration is <13.0 g/dl in males and <12.0 g/dl in females. (Not Graded)
  Diagnose anemia in children with CKD if Hb concentration is <11.0 g/dl in children 0.5-5 years, <11.5 g/dl in children 5-12 years, and <12.0 g/dl in children 12-15 years. (Not Graded)

Thus, in the present invention, optionally
  (a) the subject is an adult or child>15 years with CKD and during said period (eg, at the beginning of the $3^{rd}$ week from $D_0$) Hb concentration<13.0 g/dl (when the subject is male) or <12.0 g/dl (when the subject is female); or
  (b) the subject with CKD and during said period (eg, at the beginning of the $3^{rd}$ week from $D_0$) Hb concentration<11.0 g/dl (wherein the subject is aged 0.5-5 years), <11.5 g/dl (wherein the subject is aged 5-12 years), or <12.0 g/dl (wherein the subject is aged 12-15 years).

Optionally, the subject is a CKD patient that has a diagnosed malignancy, has suffered one or more strokes, and/or has suffered a malignancy. ESA therapy is usually to be proceeded with caution (if at all) in such patients, and thus the invention (especially ESA reducing or sparing aspects thereof) are advantageous in such subjects.

Optionally, the subject is a CKD 5D patient (eg, an human adult, eg, a male or female) with Hb concentration from 9.0 to 10.0 g/dl.

Optionally, the invention is for maintaining Hb concentration above 11.5 g/dl in an human adult patient with CKD.

Optionally, the invention is for maintaining Hb concentration from 9.0 to 13 g/dl (eg, 9.0 to 11.5 g/dl) in an adult human patient with CKD.

Optionally, the invention is for maintaining Hb concentration from 11.0 to 12 g/dl in a paediatric human patient with CKD. In an example, the patient is 15 or younger; or younger than 15; or 10 or younger.

In an example, the CKD patient is an adult male. In another example, the CKD patient is an adult female.

Optionally, the subject (eg, an adult human) is a CKD 5HD patient, a patient on hemofiltration or a patient on hemodiafiltration therapy, wherein the method comprises intravenous or subcutaneous administration of ESA.

Optionally, the subject (eg, an adult human) is a CKD ND or CKD 5PD patient, wherein the method comprises subcutaneous administration of ESA.

Optionally, before administration of the anti-BMP6 antibody of fragment, the patient is ESA hporesponsive indicated by less than 5% increase or no increase in Hb concentration after a month ESA treatment (prior to carrying out the method of the invention).

EXAMPLES

Example 1: Evaluation of BMP6 Antagonism with ESA on Haemoglobin Metabolism in a Mouse Model of Anaemia 1. Objectives Anaemia is a common complication of infections and inflammatory diseases. The purpose of the study was to evaluate the time-dependent effects of an anti-human BMP6 antibody (hereafter human antibody "KYAB1248") on baseline haemoglobin levels and on haemoglobin response to a erythropoiesis-stimulating agent, darbepoetin alfa, in a mouse model of acute anaemia induced by an injection of heat and phenol-killed *Brucella abortus* (BA) in healthy C57BL/6J male mice, as described by Kim et al, 2014 (infra). The effects of KYAB1248 were compared to those of a human IgG4 isotype control (antibody KYAB1110) that does not specifically bind BMP6.

[Kim A, Fung E, Parikh S G, Valore E V, Gabayan V, Nemeth E, and Ganz T. 2014. A mouse model of anaemia of inflammation: complex pathogenesis with partial dependence on hepcidin. Blood. 123(8), 1129-11362.]

2. Materials and Methods 2.1. Animals

The experiments were carried out using 120 male C57BL/6J mice, weighing 20-35 g (12-week old) at the beginning of the experiments.

The animals were housed in groups of 5-10 in polysulfone cages (floor area=1500 cm$^2$) under standard conditions: room temperature (22±2° C.), hygrometry (55±10%), light/dark cycle (12 h/12 h), air replacement (15-20 volumes/hour), water and food (SDS, RM1 containing nominal 159.3 mg/kg iron) ad libitum. In case of aggressive dominance, mice were isolated from the social group. The mice were acclimated to environmental conditions for at least 5 days prior to experimentation. The mice were identified by marking their tail using indelible markers. The study was conducted under EU animal welfare regulations for animal use in experimentation (European Directive 2010/63/EU).

2.2. Choice of Species

The mouse has been chosen to evaluate the effects of the antibodies as it is well established from historical literature as an appropriate non-clinical model to investigate acute markers of iron metabolism, including serum iron, hepcidin gene expression and tissue levels of non-heme iron (Andriopoulos et al., 2009, supra). Moreover BA-induced model of anaemia was developed using C57BL/6J mice, as described by Kim et al. (Kim et al., 2014, supra).

2.3. Preparation of *Brucella abortus* Suspension

A concentrated suspension of *Brucella abortus* (Weybridge 99 Strain) inactivated by heat and phenol was used to induce anaemia in mice (Pourquier Wright's serum agglutination brucellosis antigen, ref P00110, Idexx). This suspension was stored at 5±3° C. until preparation of a concentrated suspension. BA suspension was centrifuged at 15,000 g for 15 minutes at room temperature. Pellet was resuspended in sterile PBS (ref 14190-094, Gibco) so that to obtain a 50× concentrated BA suspension. Aliquots were prepared and stored at −80° C. until use. On the day of administration, this suspension was diluted in sterile PBS to the desired concentration of 10×.

2.4. Administration Protocol

Mice were randomly allocated to one of the treatment groups (N=4 per group) and administered according to the treatment schedule described in the table 6 below.

Heat and phenol-killed BA was administered as a single intraperitoneal (ip) injection of a fixed volume of 200 μL of a 10× concentrated BA suspension per mouse (on day 0). In the "predose" group, mice were not dosed with the BA suspension. In the "ESA on day 1" group, mice received an ip administration of PBS (200 μL) instead of the BA suspension.

The intravenous (iv) route of administration was used to evaluate the effects of KYAB1248 in comparison with those of KYAB1110 hIgG4 isotype control since it is the intended clinical route. Each administration of KYAB1110 and KYAB1248 was performed on day 0 and day 6 as a tail vein bolus iv injection of the antibody solution at the dose of 10 mg/kg body weight under a volume of 5 mL/kg body weight. Each mouse was weighed prior to dosing. The doses of KYAB1248 and KYAB1110 were chosen according to the known pharmacological profile of each antibody.

In the "predose" group, mice were not dosed with any antibody. In the "ESA on day 1" group, mice received an iv administration of PBS (under a volume of 5 mL/kg body weight) instead of KYAB1110 or KYAB1248.

For the day 0 dosing, the BA suspension was administered first and then followed immediately with the KYAB1248 or KYAB1110 antibody iv injection, within a 5 minute window.

ESA (Darbepoetin alfa, Aranesp®, Amgen) was administered as a single subcutaneous (sc) injection at the dose of 100 μg/kg body weight under a volume of 10 mL/kg body weight on day 1 or day 7 (24 hours after antibody administration). Each mouse was weighed prior to dosing.

TABLE 6

Treatment schedule

| | | Day 0 | | | | | | | | | | | | |
|---|---|---|---|---|---|---|---|---|---|---|---|---|---|---|
| | | T0 | | | | | | | | | | Day 14 | Day 21 | Day 28 |
| | | | | | T6h | Day 1 | | | Day 7 | | Day 8 | | | |
| | Number of animals | ip | iv | Terminal blood collection | Terminal blood collection | sc | Terminal blood collection | Day 6 iv | sc | Terminal blood collection | Terminal blood collection | Terminal blood collection | Terminal blood collection | Terminal blood collection |
| Predose | N = 4 | | | X | | | | | | | | | | |
| ESA on day 1 | N = 4 | PBS | PBS | | | ESA | | PBS | | | X | | | |

TABLE 6-continued Treatment schedule

| | Number of animals | Day 0 T0 ip | Day 0 T0 iv | Day 0 T0 Terminal blood collection | T6h Terminal blood collection | Day 1 sc | Day 1 Terminal blood collection | Day 6 iv | Day 7 sc | Day 7 Terminal blood collection | Day 8 Terminal blood collection | Day 14 Terminal blood collection | Day 21 Terminal blood collection | Day 28 Terminal blood collection |
|---|---|---|---|---|---|---|---|---|---|---|---|---|---|---|
| KYAB1110 | N = 4 | BA 10x | KYAB1110 | X | | | | | | | | | | |
| | N = 4 | BA 10x | KYAB1110 | | | | X | | | | | | | |
| | N = 4 | BA 10x | KYAB1110 | | | | | KYAB1110 | | X | | | | |
| | N = 4 | BA 10x | KYAB1110 | | | | | KYAB1110 | | | | X | | |
| | N = 4 | BA 10x | KYAB1110 | | | | | KYAB1110 | | | | | X | |
| | N = 4 | BA 10x | KYAB1110 | | | | | KYAB1110 | | | | | | X |
| KYAB1248 | N = 4 | BA 10x | KYAB1248 | X | | | | | | | | | | |
| | N = 4 | BA 10x | KYAB1248 | | | | X | | | | | | | |
| | N = 4 | BA 10x | KYAB1248 | | | | | KYAB1248 | | X | | | | |
| | N = 4 | BA 10x | KYAB1248 | | | | | KYAB1248 | | | | X | | |
| | N = 4 | BA 10x | KYAB1248 | | | | | KYAB1248 | | | | | X | |
| | N = 4 | BA 10x | KYAB1248 | | | | | KYAB1248 | | | | | | X |
| KYAB1110 + ESA on day 1 | N = 4 | BA 10x | KYAB1110 | | | ESA | | KYAB1110 | | X | | | | |
| | N = 4 | BA 10x | KYAB1110 | | | ESA | | KYAB1110 | | | | X | | |
| | N = 4 | BA 10x | KYAB1110 | | | ESA | | KYAB1110 | | | | | X | |
| | N = 4 | BA 10x | KYAB1110 | | | ESA | | KYAB1110 | | | | | | X |
| KYAB1248 + ESA on day 1 | N = 4 | BA 10x | KYAB1248 | | | ESA | | KYAB1248 | | X | | | | |
| | N = 4 | BA 10x | KYAB1248 | | | ESA | | KYAB1248 | | | | X | | |
| | N = 4 | BA 10x | KYAB1248 | | | ESA | | KYAB1248 | | | | | X | |
| | N = 4 | BA 10x | KYAB1248 | | | ESA | | KYAB1248 | | | | | | X |
| KYAB1110 + ESA on day 7 | N = 4 | BA 10x | KYAB1110 | | | | | KYAB1110 | ESA | X | | | | |
| | N = 4 | BA 10x | KYAB1110 | | | | | KYAB1110 | ESA | | | X | | |
| | N = 4 | BA 10x | KYAB1110 | | | | | KYAB1110 | ESA | | | | X | |
| | N = 4 | BA 10x | KYAB1110 | | | | | KYAB1110 | ESA | | | | | X |
| KYAB1248 + ESA on day 7 | N = 4 | BA 10x | KYAB1248 | | | | | KYAB1248 | ESA | X | | | | |
| | N = 4 | BA 10x | KYAB1248 | | | | | KYAB1248 | ESA | | | X | | |
| | N = 4 | BA 10x | KYAB1248 | | | | | KYAB1248 | ESA | | | | X | |
| | N = 4 | BA 10x | KYAB1248 | | | | | KYAB1248 | ESA | | | | | X |

2.5. Parameters

Clinical signs were evaluated. Haemoglobin was measured in all animals except one from the 'KYAB1248+ESA on day 7' dose group (Day 8 sacrifice).

2.6. Terminal Procedure 2.6.1. Terminal Blood Collection

Terminal procedure was performed at the indicated time points (i.e. 6 hours, 24 hours, on days 7, 8, 14, 21 and 28 post-dose) with the group numbers indicated in the above table. Predose group (TO, non-administered mice) was also sacrificed.

At the end of the experiments, i.e. at each time point, all animals was anaesthetised with pentobarbital (180 mg/kg, ip) and venous blood was collected using cardiac puncture. Whole blood was immediately placed in lithium heparinised collection tubes as described below. Collection tubes was gently mixed. The exact time of blood sampling was noted for each animal. A minimum volume of 0.2 mL of non hemolysed whole blood was placed in a first lithium heparinized collection tube for standard haematology assessment.

Each test Item formulation was freshly prepared under sterile conditions on the day of dosing. For each antibody, a solution at the concentration of 2 mg/mL is needed to administer animals at the dose of 10 mg/kg. This solution was obtained by dilution of the 10 mg/mL stock solution in vehicle (sterile endotoxin tested PBS (Life Technologies, Product 10010023)) with a 1:5 dilution ratio.

3. Results

In BA inoculated animals receiving antibody doses only (i.e. without ESA administration) there was no observed difference in the blood haemoglobin anaemia profiles between KYAB1248 and the hIgG4 isotype control groups (FIG. 1).

The administration of ESA to BA treated animals dosed with isotype control antibody had no impact on haemoglobin levels and the severity of the anaemia (day 14 mean haemoglobin results of 8.1, 7.8 and 8.2 g/dL for groups 'no ESA' (see FIG. 1), 'ESA day 1' (see FIG. 2) and 'ESA day 7' (see FIG. 3), respectively).

Figure 2:
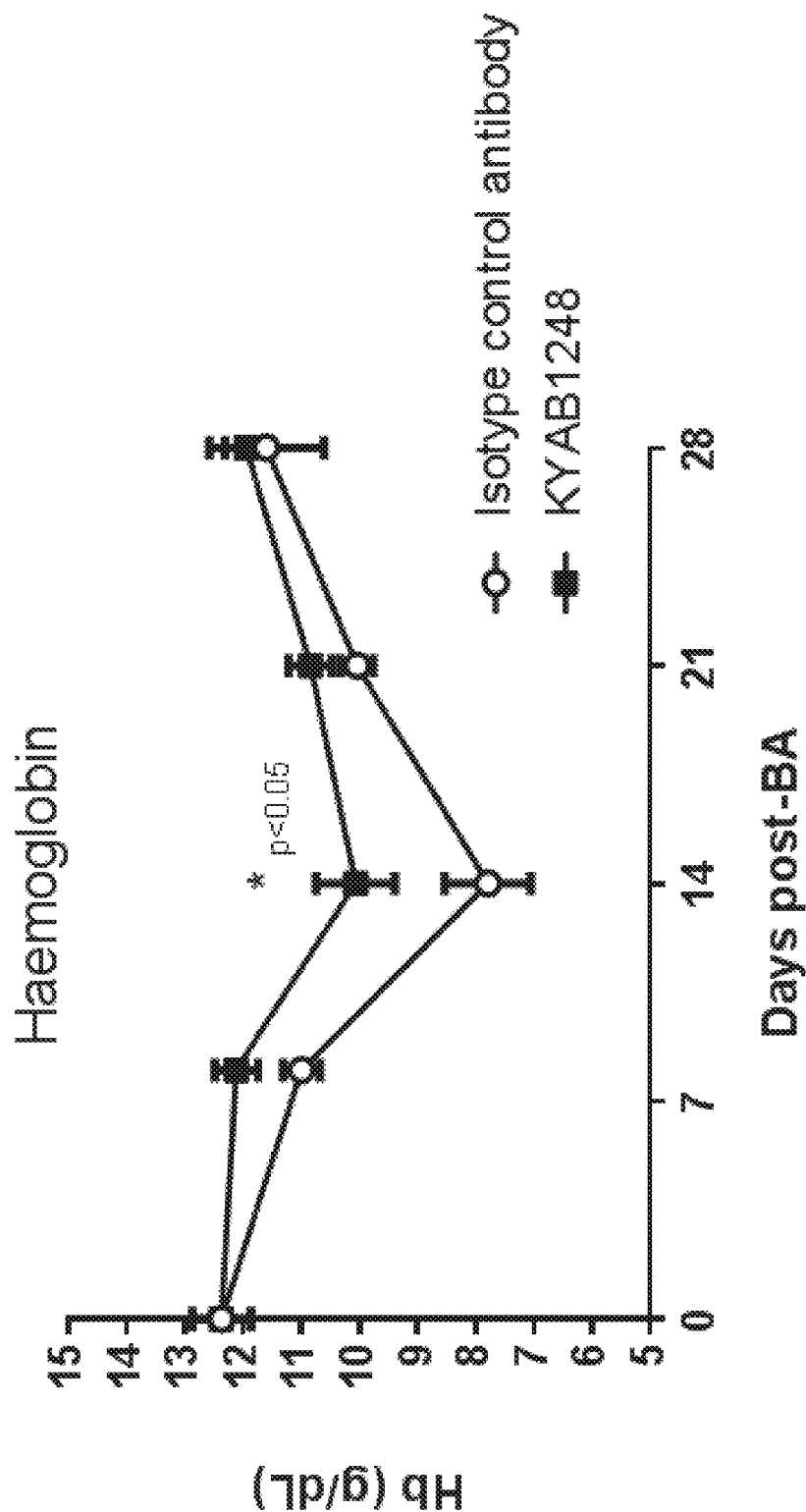
FIG. 2: Haemoglobin levels in murine Brucella model—antibody 10 mg/kg Day 0 & 6, ESA at day 1.
Figure 3:
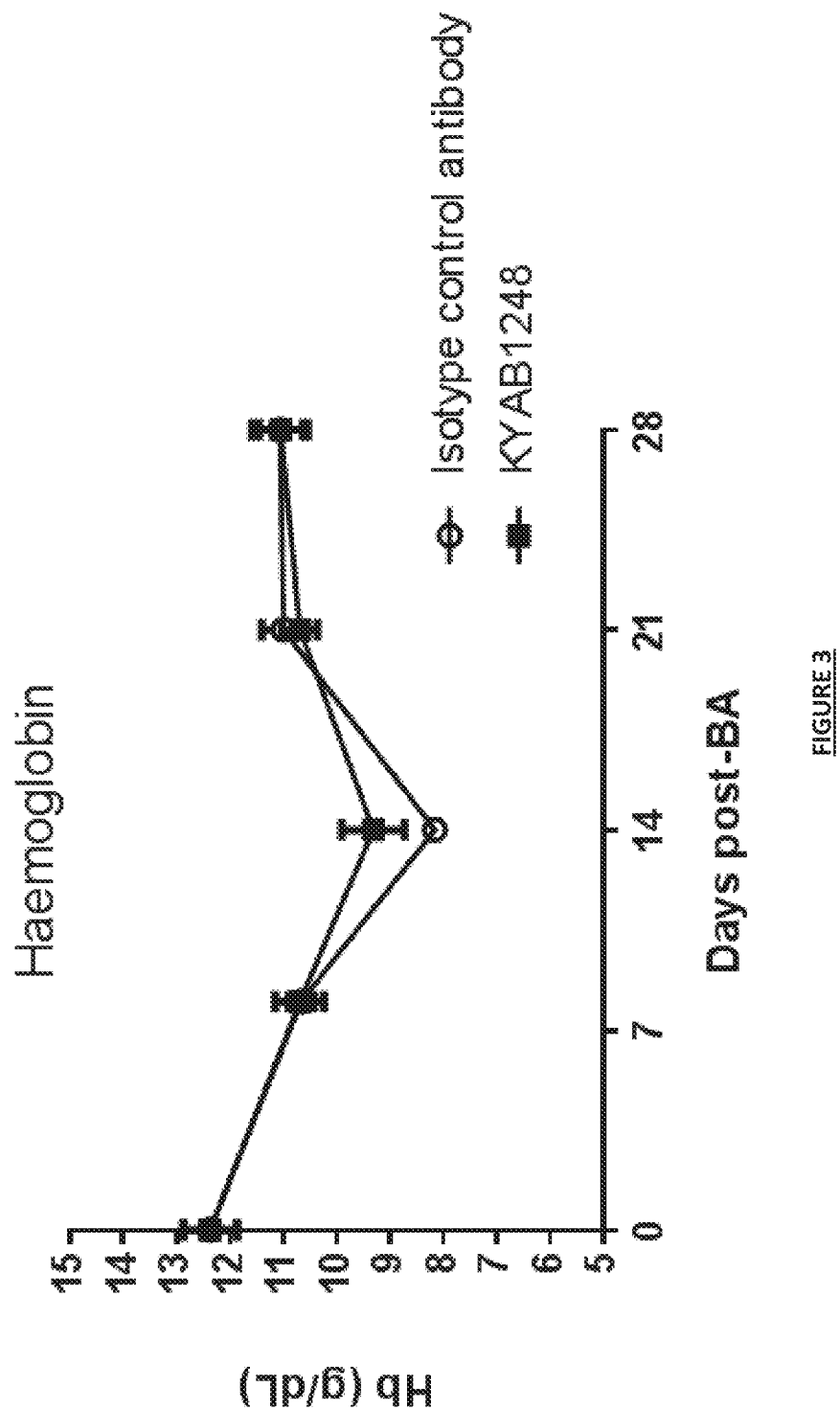
FIG. 3: Haemoglobin levels in murine Brucella model—antibody 10 mg/kg Day 0 & 6, ESA at day 7.

Changes in blood haemoglobin and improvements in anaemia were achieved in animals receiving KYAB1248 antibody and ESA however. This effect was most pronounced in animals dosed with ESA on Day 1, i.e. 24 hours after the BA injection and the first KYAB1248 antibody injection (FIG. 2). Higher mean levels of haemoglobin relative to isotype control dosed animals were recorded at each post-BA timepoint tested (days 8, 14, 21 and 28) and reached statistical significance at the haemoglobin nadir timepoint of day 14 (7.8 g/dL (isotype antibody+ESA) vs. 10.1 g/dL (KYAB1248+ESA), $p<0.05$ ANOVA). An increase in day 14 mean haemoglobin levels, although not statistically significant, was also seen in KYAB1248 antibody dosed animals that received the ESA injection on day 7, i.e. at a point when the anaemia had already developed (9.3 g/dL (KYAB1248+ESA) vs. 8.2 g/dL (isotype antibody+ESA)).

Example 2: Maintenance & Statistically Significant Increase in Haemoglobin Concentration and Demonstration of Mean Corpuscular Haemoglobin (MCH) in Anti-BMP6/ESA Versus Anti-BMP6 Alone in a Treatment Model of Anaemia of Chronic Disease (ACD)

Female Lewis rats were kept on a standard rodent diet until they reached an age of 6 to 8 weeks and a body weight of 140 to 160 g. All treatments were performed by intraperitoneal (i.p.) or subcutaneous (s.c.) injection. Chronic inflammation (arthritis) causing ACD was induced using an i.p. injection of a group A streptococcal peptidoglycan-polysaccharide (PG-APS) (Lee Laboratories, Grayson, Ga., USA) at a total dose of 15 µg rhamnose/g body weight.

Figure 4:
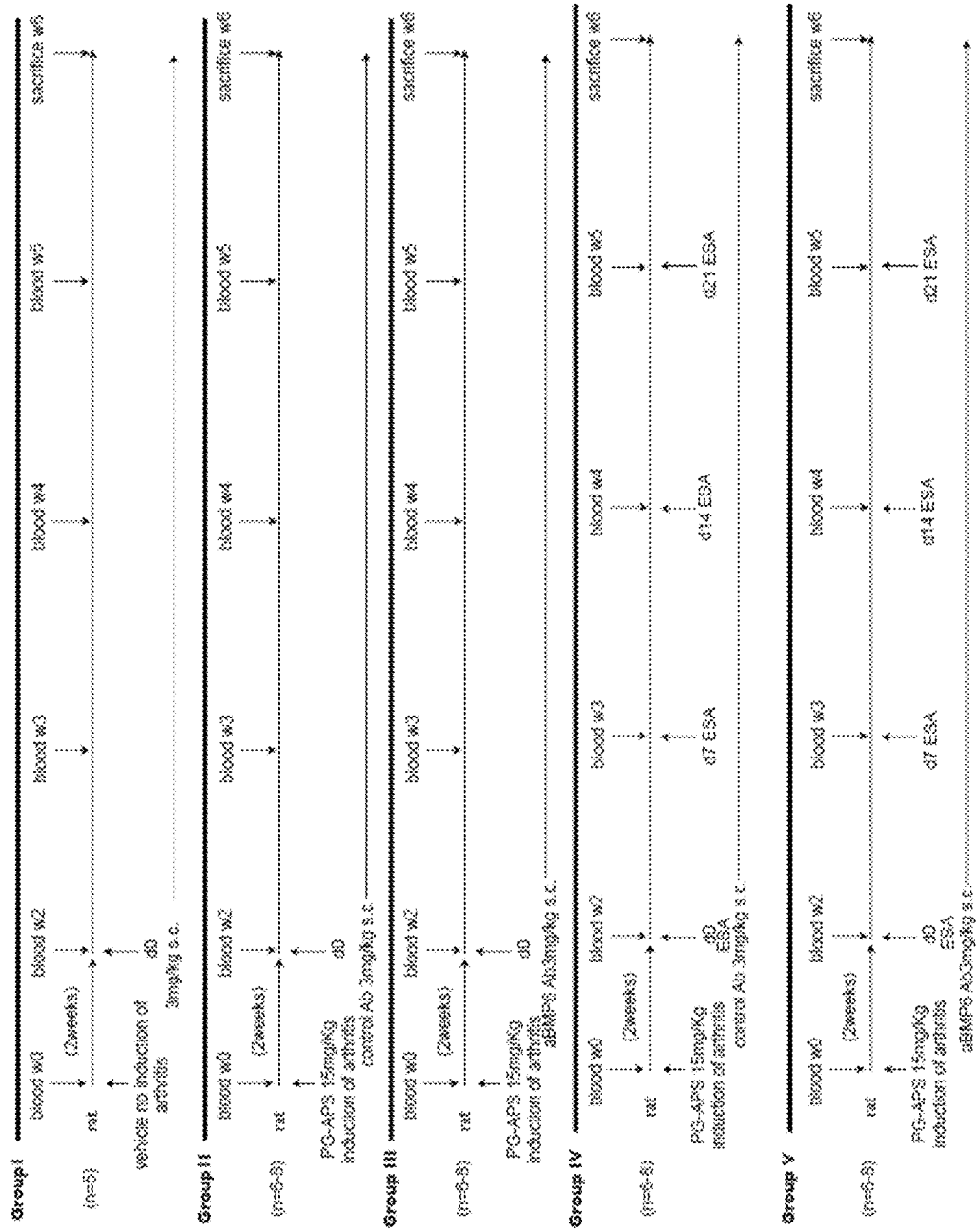
FIG. 4: Treatment schematic.

Rats responding to PG-APS injection determined by development of arthritis and increased neutrophil count were randomized into 4 different groups. Treatment was started 2 weeks after PG-APS injections (day $0=D_0$). FIG. 4 shows the treatment schedule as follows:—

Group 1: Non inflamed control rats (did not receive PG-APS) with a single s.c. injection of an IgG4 Isotype control antibody [3 mg/kg] at $D_0$. The control was a humanised IgG4 antibody that does not specifically bind to BMP6.

Group 2: ACD rats (ie, rats with ACD) with a single s.c. injection of IgG4 Isotype control antibody [3 mg/kg] at $D_0$.

Group 3: ACD rats with a single s.c. injection of an anti-BMP6 IgG4 antibody [3 mg/kg] at $D_0$.

Group 4: ACD rats with a single s.c. injection of IgG4 Isotype control antibody [3 mg/kg] at $D_0$. And a single s.c. darbepoetin alfa (ARANESP®, Amgen Inc) Injection, at a dose of 10 µg/kg body weight, once weekly. A total of 4 such darbepoetin alfa injections.

Group 5: ACD rats with a single s.c. injection of an anti-BMP6 IgG4 antibody [3 mg/kg] at $D_0$. And a single s.c. darbepoetin alfa injection, at a dose of 10 µg/kg body weight, once weekly. A total of 4 such darbepoetin alfa injections.

The experiment was terminated after 4 weeks of treatment (6 weeks after PG-APS application) and rats were sacrificed. For determination of haemoglobin levels (over time, small blood samples (300 µL) were taken weekly by tail vein puncture from every animal.

After 4 treatment weeks animals were sacrificed and the experiment terminated.

The anti-BMP6 antibody (test antibody) is one that competes in a HTRF assay with a reference antibody for binding human BMP6 (or binds the same epitope of human BMP6 as the reference antibody), wherein the reference antibody comprises heavy chains each comprising the amino acid sequence of SEQ ID NO: 1 or 2, and light chains each comprising the amino acid sequence of SEQ ID NO: 3, wherein the assay uses the test antibody labelled with a donor label (Eu3+cryptate) and a human BMP6 labelled with an acceptor fluorophore AlexaFluor™ 647 to enable energy transfer between donor and acceptor, wherein said competition between the antibodies is detected by a reduction in fluorescence signal of at least 20% when the test antibody is in the presence of the reference antibody versus signal without the reference antibody.

The anti-BMP6 antibody (test antibody) is one that competes in a HTRF assay with a reference antibody for binding human BMP6 (or binds the same epitope of human BMP6 as the reference antibody), wherein the reference antibody comprises heavy chains each comprising the amino acid sequence of SEQ ID NO: 4, and light chains each comprising the amino acid sequence of SEQ ID NO: 5, wherein the assay uses the test antibody labelled with a donor label (Eu3+cryptate) and a human BMP6 labelled with an acceptor fluorophore AlexaFluor™ 647 to enable energy transfer between donor and acceptor, wherein said competition between the antibodies is detected by a reduction in fluorescence signal of at least 20% when the test antibody is in the presence of the reference antibody versus signal without the reference antibody.

Results

Figure 5:
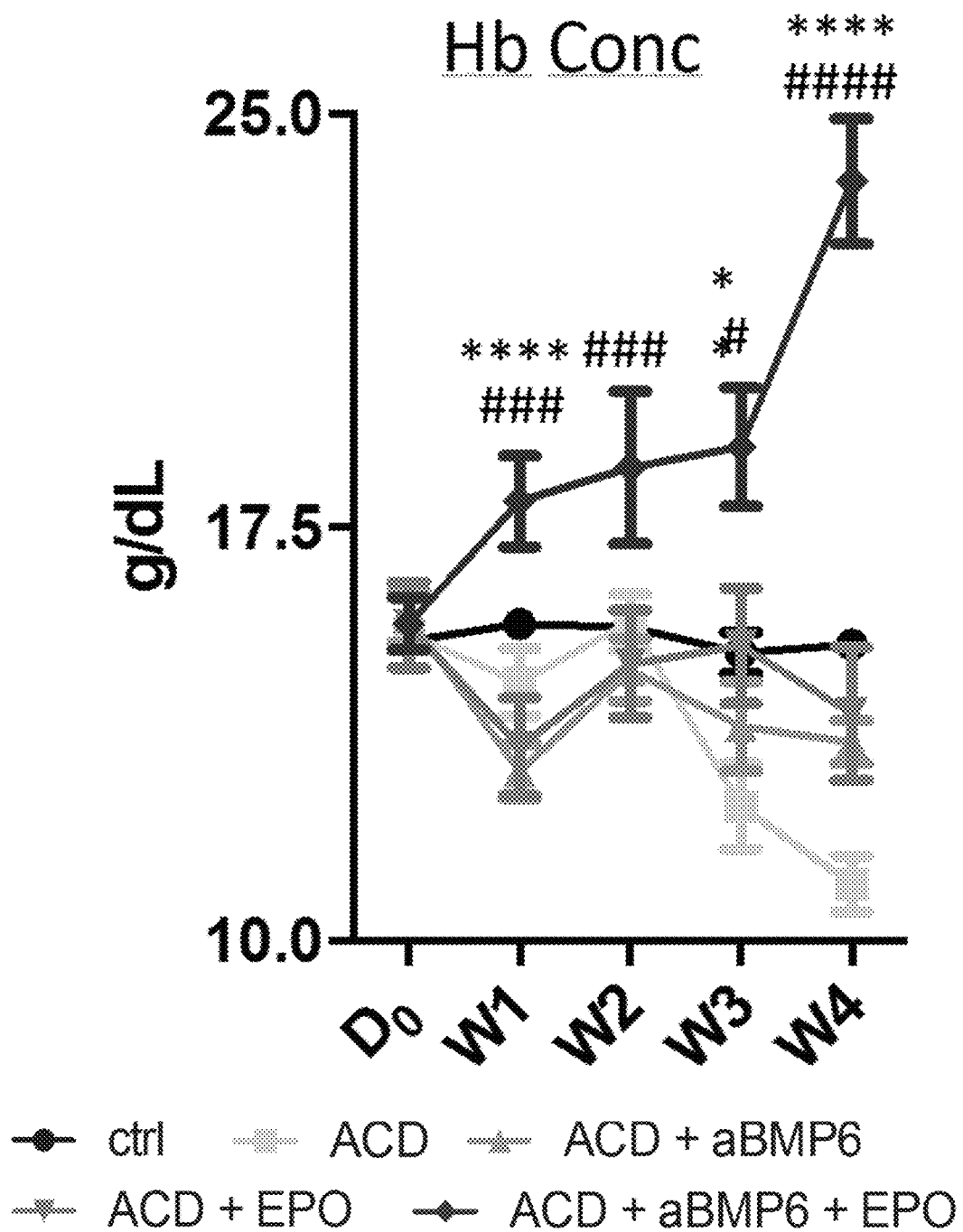
FIG. 5: Haemoglobin concentrations.
Figure 6:
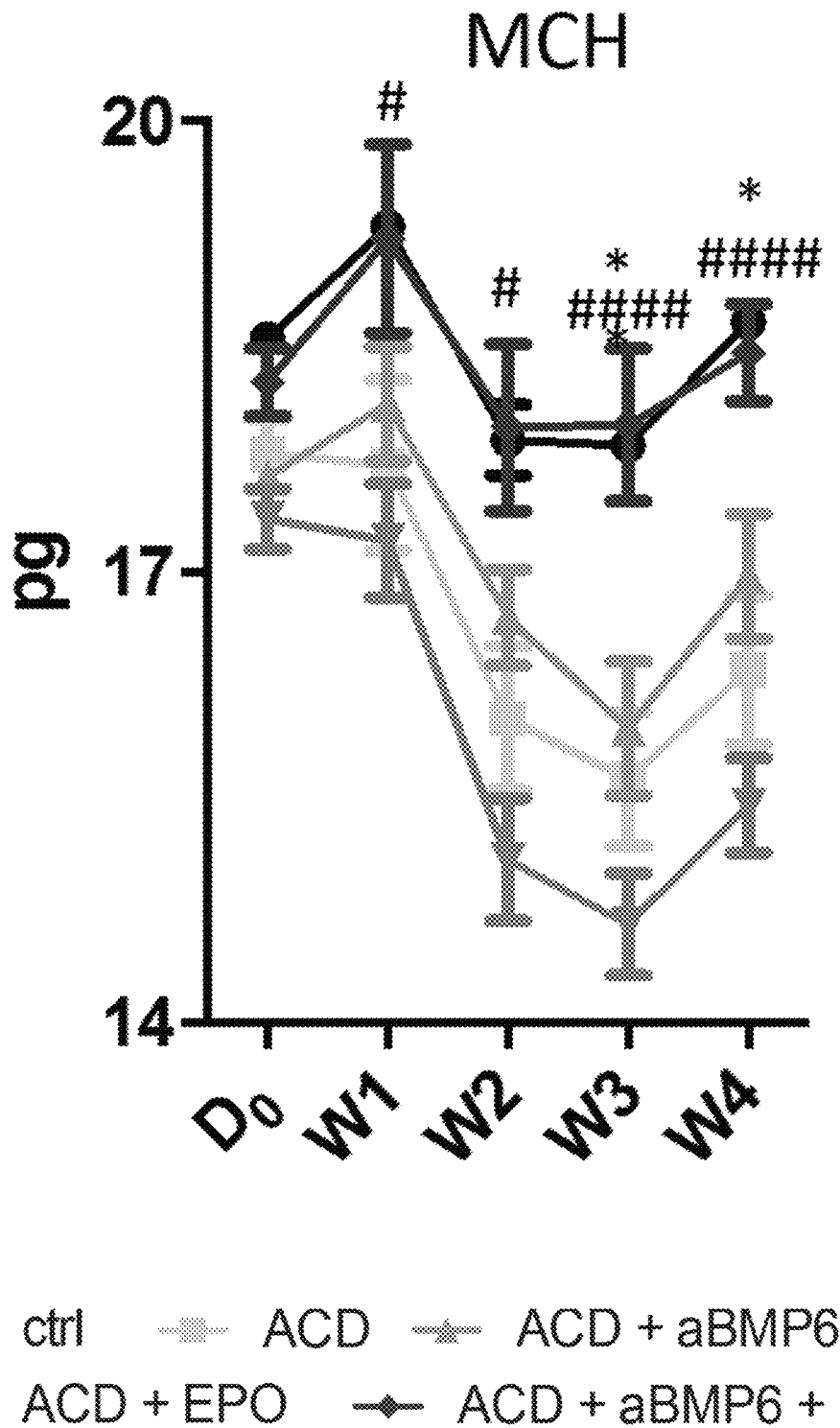
FIG. 6: Mean corpuscular haemoglobin (MCH) levels.

Reference is made to FIGS. 5 and 6, which show blood Hb concentrations and MHC levels in the experimental groups.

Statistics: Anova with Dunnett's multiple comparison test was used.

*=Comparing rats receiving anti-BMP6 antibody alone versus rats receiving anti-BMP6 antibody+ESA

**** $p<0.0001$

*** $p<0.001$

** $p<0.01$

* $p<0.05$

=Comparing rats receiving ESA alone versus rats receiving anti-BMP6 antibody+ESA

$p<0.0001$

$p<0.001$

$p<0.01$

$p<0.05$

TABLE 7

Average Hb Concentrations - ESA + Anti-BMP6 Antibody (Group 5)

| $D_0$ (Baseline) Last Day of Week (W) | 15.75 Average Hb Concentration (g/dl) | Increase in Hb Conc. Over Baseline | % of Baseline Hb Conc. |
|---|---|---|---|
| 1 | 17.98 | +2.23 | 114 |
| 2 | 18.59 | +2.84 | 118 |
| 3 | 18.96 | +3.21 | 120 |
| 4 | 23.78 | +8.03 | 151 |

There is a 125% increase in Hb concentration from the end of W3 to the end of W4.

TABLE 8

Average Hb Concentrations - Anti-BMP6 Antibody (Group 3, no ESA)

| $D_0$ (Baseline) Last Day of Week (W) | 15.88 Average Hb Concentration (g/dl) | Increase in Hb Conc. Over Baseline | % of Baseline Hb Conc. |
|---|---|---|---|
| 1 | 13.07 | −2.81 | 82 |
| 2 | 14.92 | −0.96 | 94 |
| 3 | 13.88 | −2.00 | 87 |
| 4 | 13.60 | −2.28 | 86 |

At the end of W3, the Hb concentration in the antibody+ESA group was 137% of the Hb concentration with antibody alone.

At the end of W4, the Hb concentration in the antibody+ESA group was 175% of the Hb concentration with antibody alone.

Hb concentration at the end of W4 is significantly higher in the antibody+ESA group than in the antibody alone group, as determined by a p-value of $p<0.0001$.

TABLE 9

Average Hb Concentrations - ESA (Group 4, no Anti-BMP6 Antibody)

| $D_0$ (Baseline) Last Day of Week (W) | 15.73 Average Hb Concentration (g/dl) | Increase in Hb Conc. Over Baseline | % of Baseline Hb Conc. |
|---|---|---|---|
| 1 | 13.53 | −2.20 | 86 |
| 2 | 15.03 | −0.70 | 96 |
| 3 | 15.36 | −0.37 | 98 |
| 4 | 14.13 | −1.60 | 90 |

At the end of W3, the Hb concentration in the antibody+ESA group was 123% of the Hb concentration with ESA alone.

At the end of W4, the Hb concentration in the antibody+ESA group was 168% of the Hb concentration with ESA alone.

Hb concentration at the end of W4 is significantly higher in the antibody+ESA group than in the ESA alone group, as determined by a p-value of $p<0.0001$.

TABLE 10

Mean Corpuscular Haemoglobin (MCH) - ESA + Anti-BMP6 Antibody (Group 5)

| $D_0$ (Baseline) Last Day of Week (W) | 18.27 Average MCH (pg) | Increase in MCH Over Baseline | % of Baseline MCH |
|---|---|---|---|
| 1 | 19.22 | +0.95 | 105 |
| 2 | 17.96 | −0.31 | 98 |
| 3 | 17.98 | −0.29 | 98 |
| 4 | 18.46 | +0.19 | 101 |

TABLE 11

Mean Corpuscular Haemoglobin (MCH) - Anti-BMP6 Antibody (Group 3, no ESA)

| $D_0$ (Baseline) Last Day of Week (W) | 17.64 Average MCH (pg) | Increase in MCH Over Baseline | % of Baseline MCH |
|---|---|---|---|
| 1 | 18.12 | +0.48 | 103 |
| 2 | 16.70 | −0.94 | 95 |
| 3 | 15.96 | −1.68 | 90 |
| 4 | 16.97 | −0.67 | 96 |

At the end of W3, the MCH in the antibody+ESA group was 113% of the MCH with antibody alone.

At the end of W4, the MCH in the antibody+ESA group was 109% of the MCH with antibody alone.

TABLE 12

Mean Corpuscular Haemoglobin (MCH) - ESA (Group 4, no Anti-BMP6 Antibody)

| $D_0$ (Baseline) Last Day of Week (W) | 17.35 Average MCH (pg) | Increase in MCH Over Baseline | % of Baseline MCH |
|---|---|---|---|
| 1 | 17.21 | −0.14 | 99 |
| 2 | 15.09 | −2.26 | 87 |
| 3 | 14.66 | −2.69 | 85 |
| 4 | 15.45 | −1.9 | 89 |

At the end of W3, the MCH in the antibody+ESA group was 123% of the MCH with ESA alone.

At the end of W4, the MCH in the antibody+ESA group was 119% of the MCH with ESA alone.

MCH at the end of W3 is significantly higher in the antibody+ESA group than in the ESA alone group, as determined by a p-value of p<0.0001.

MCH at the end of W4 is significantly higher in the antibody+ESA group than in the ESA alone group, as determined by a p-value of p<0.0001.

The results demonstrated that a combination of anti-BMP6 antibody and ESA (Group 5) could be used to treat subjects that had established anaemia. The combination treatment maintained Hb concentration above the baseline value throughout the 3 and 4 week periods (counted from $D_0$) and at the end of the 4 week period Hb concentration had risen more than 8 g/dl from baseline. This was a highly significant result (as determined by a p-value of p<0.0001) compared to the administration of anti-BMP6 antibody alone (Group 3), and we believe that this would support the ability to lower or spare ESA dosing below conventional amounts (thus minimising side effects of ESA). Hb concentration at the end of the treatment period was also significantly higher with the combination treatment compared with ESA alone (as determined by a p-value of p<0.0001).

In the combination group there was a 25% increase even towards the end of the period (in the $4^{th}$ week following the antibody administration), which was not observed in any other treatment group.

Significant improvements were also seen in MCH when comparing the combination treatment with ESA alone, both at the end of the $3^{rd}$ and $4^{th}$ weeks (as determined by a p-value of p<0.0001). Importantly, the MCH in the combination group was not significantly diminished. We believe, therefore, that in the combination group the enhanced Hb concentration is productively used in increased erythropoiesis (as indicated by increased Hb concentration and no significant diminishment in MCH).

The invention claimed is:

1. A method of treating anemia in a subject suffering from rheumatoid arthritis, the method comprising
- (a) on an initial day ($D_0$) administering to the subject an anti-Bone Morphogenetic Protein 6 (BMP6) antibody or antigen-binding fragment thereof; and
- (b) in a treatment period of at least 3 consecutive weeks, said period starting on $D_0$, administering a plurality of doses of an erythropoietin stimulating agent (ESA), wherein the ESA is an erythropoietin or a hypoxia-inducible factor prolyl-hydroxylase (HIF-PH) inhibitor, and wherein the anti-BMP6 antibody or antigen-binding fragment thereof comprising a light chain variable region (LCVR) and a heavy chain variable region (HCVR), and wherein:
  - (i) the HCVR comprises a heavy chain complementarity determining region (HCDR) HCDR1 comprising the amino acid sequence of GYTFTSYAMH (SEQ ID NO: 20), an HCDR2 comprising the amino acid sequence of YINPYNDGTKYNENFKG (SEQ ID NO: 21), and an HCDR3 comprising the amino acid sequence of RPFGNAMDI (SEQ ID NO:22); and the LCVR comprises a light chain complementarity determining region (LCDR) LCDR1 comprising the amino acid sequence of RSSENIYRNLA (SEQ ID NO: 23), an LCDR2 comprising the amino acid sequence of AATNLAD (SEQ ID NO: 24), and an LCDR3 comprising the amino acid sequence of QGIWGTPLT (SEQ ID NO: 25);
  - (ii) the HCVR comprises an HCDR1 comprising the amino acid sequence of SEQ ID NO: 20, an HCDR2 comprising the amino acid sequence of YINPYNRGTKYNENFKG (SEQ ID NO: 26), and an HCDR3 comprising the amino acid sequence of SEQ ID NO:22; and the LCVR comprises an LCDR1 comprising the amino acid sequence of SEQ ID NO: 23, an LCDR2 comprising the amino acid sequence of SEQ ID NO: 24, and an LCDR3 comprising the amino acid sequence of SEQ ID NO: 25;
  - (iii) the HCVR comprises HCDR1, HCDR2 and HCDR3 of a heavy chain comprising the amino acid sequence of SEQ ID NO: 4; and the LCVR comprises LCDR1, LCDR2, and LCDR3 of a light chain comprising the amino acid sequence of SEQ ID NO: 5;
  - (iv) the HCVR comprises an HCDR1 comprising the amino acid sequence of SYVVH (SEQ ID NO: 27), an HCDR2 comprising the amino acid sequence of RIRLETHGYAAEYAASVKG (SEQ ID NO: 28), and an HCDR3 comprising the amino acid sequence of VERSKSGFDN (SEQ ID NO:29); and the LCVR comprises an LCDR1 comprising the amino acid sequence of TGSSSNIGAGYSVH (SEQ ID NO: 30), an LCDR2 comprising the amino acid sequence of GQSERPS (SEQ ID NO: 31), and an LCDR3 comprising the amino acid sequence of QSWDSSQTLVV (SEQ ID NO: 32);
  - (v) the HCVR comprises an HCDR1 comprising the amino acid sequence of GFTFSSY (SEQ ID NO: 33), an HCDR2 comprising the amino acid sequence of RLETHGYA (SEQ ID NO: 34), and an HCDR3 comprising the amino acid sequence of VERSKSGFDN (SEQ ID NO:35); and the LCVR comprises an LCDR1 comprising the amino acid sequence of SSSNIGAGYS (SEQ ID NO: 36), an LCDR2 comprising the amino acid sequence of GQS (SEQ ID NO: 37), and an LCDR3 comprising the amino acid sequence of WDSSQTLV (SEQ ID NO: 38);
  - (vi) the HCVR comprises an HCDR1 comprising the amino acid sequence of SYVVH (SEQ ID NO: 39), an HCDR2 comprising the amino acid sequence of RIKRESSSYTTMYAAPVKG (SEQ ID NO: 40), and an HCDR3 comprising the amino acid sequence of VERSKSGFDN (SEQ ID NO:41); and the LCVR comprises an LCDR1 comprising the amino acid sequence of TGSSSNIGAGYSVH (SEQ ID NO: 42), an LCDR2 comprising the amino acid sequence of GQSERPS (SEQ ID NO: 43), and an LCDR3 comprising the amino acid sequence of QSWDSSQTLVV (SEQ ID NO: 45);
  - (vii) the HCVR comprises an HCDR1 comprising the amino acid sequence of GFTFSSY (SEQ ID NO: 46), an HCDR2 comprising the amino acid sequence of KRESSSYT (SEQ ID NO: 47), and an HCDR3 comprising the amino acid sequence of VERSKSGFDN (SEQ ID NO:48); and the LCVR comprises an LCDR1 comprising the amino acid sequence of SSSNIGAGYS (SEQ ID NO: 49), an LCDR2 comprising the amino acid sequence of GQS (SEQ ID NO: 50), and an LCDR3 comprising the amino acid sequence of WDSSQTLV (SEQ ID NO: 51);
  - (viii) the HCVR comprises an HCDR1 comprising the amino acid sequence of SYVVH (SEQ ID NO: 52), an HCDR2 comprising the amino acid sequence of RTRHSDMGYATSYAAPVKG (SEQ ID NO: 53), and an HCDR3 comprising the amino acid sequence of VERSKSGFDN (SEQ ID NO: 54); and the LCVR comprises an LCDR1 comprising the amino acid sequence of TGSSSNIGAGYSVH (SEQ ID NO: 55), an LCDR2 comprising the amino acid sequence of GQSERPS (SEQ ID NO: 56), and an LCDR3 comprising the amino acid sequence of QSWDSSQTLVV (SEQ ID NO: 57);

(ix) the HCVR comprises an HCDR1 comprising the amino acid sequence of GFTFSSY (SEQ ID NO: 58), an HCDR2 comprising the amino acid sequence of RHSDMGYA (SEQ ID NO: 59), and an HCDR3 comprising the amino acid sequence of VERSKSGFDN (SEQ ID NO: 60); and the LCVR comprises an LCDR1 comprising the amino acid sequence of SSSNIGAGYS (SEQ ID NO: 61), an LCDR2 comprising the amino acid sequence of GQS (SEQ ID NO: 62), and an LCDR3 comprising the amino acid sequence of WDSSQTLV (SEQ ID NO: 63);

(x) the HCVR comprises an HCDR1 comprising the amino acid sequence of SYVVH (SEQ ID NO: 64), an HCDR2 comprising the amino acid sequence of RIKDHKQGYTTAYAASVKG (SEQ ID NO: 65), and an HCDR3 comprising the amino acid sequence of VERSKSGFDN (SEQ ID NO: 66); and the LCVR comprises an LCDR1 comprising the amino acid sequence of TGSSSNIGAGYSVH (SEQ ID NO: 67), an LCDR2 comprising the amino acid sequence of GSSERPS (SEQ ID NO: 68), and an LCDR3 comprising the amino acid sequence of QSWDSSQTLVV (SEQ ID NO: 69); or (xi) the HCVR comprises an HCDR1 comprising the amino acid sequence of GFTFSSY (SEQ ID NO: 70), an HCDR2 comprising the amino acid sequence of KDHKQGYT (SEQ ID NO: 71), and an HCDR3 comprising the amino acid sequence of VERSKSGFDN (SEQ ID NO: 72); and the LCVR comprises an LCDR1 comprising the amino acid sequence of SSSNIGAGYS (SEQ ID NO: 73), an LCDR2 comprising the amino acid sequence of GSS (SEQ ID NO: 74), and an LCDR3 comprising the amino acid sequence of WDSSQTLV (SEQ ID NO: 75).

2. The method of claim 1, wherein:
(i) the subject is refractory or non-responsive to an ESA;
(ii) the subject has high blood pressure;
(iii) the subject has or has had pure red cell aplasia; or
(iv) the dose of the ESA is less than a conventional dose of the ESA for the subject in the absence of the anti-BMP6 antibody or antigen-binding fragment thereof.

3. The method of claim 2, wherein the subject is refractory or non-responsive to an ESA.

4. The method of claim 3, wherein the ESA is darbepoetin alfa or epoetin alfa.

5. The method of claim 2, wherein the subject has high blood pressure.

6. The method of claim 2, wherein the subject has or has had pure red cell aplasia.

7. The method of claim 6, wherein the red cell aplasia is caused by receiving an ESA.

8. The method of claim 7, wherein the ESA is darbepoetin alfa or epoetin alfa.

9. The method of claim 2, wherein the dose of the ESA is less than a conventional dose of the ESA for the subject in the absence of the anti-BMP6 antibody or antigen-binding fragment thereof.

10. The method of claim 1, wherein the HCVR comprises an HCDR1 comprising the amino acid sequence of SEQ ID NO: 20, an HCDR2 comprising the amino acid sequence of SEQ ID NO: 21, and an HCDR3 comprising the amino acid sequence of SEQ ID NO:22; and the LCVR comprises an LCDR1 comprising the amino acid sequence of SEQ ID NO: 23, an LCDR2 comprising the amino acid sequence of SEQ ID NO: 24, an LCDR3 comprising the amino acid sequence of SEQ ID NO: 25.

11. The method of claim 1, wherein the HCVR comprises an HCDR1 comprising the amino acid sequence of SEQ ID NO: 20, an HCDR2 comprising the amino acid sequence of SEQ ID NO: 26, and an HCDR3 comprising the amino acid sequence of SEQ ID NO:22; and the LCVR comprises an LCDR1 comprising the amino acid sequence of SEQ ID NO: 23, an LCDR2 comprising the amino acid sequence of SEQ ID NO: 24, an LCDR3 comprising the amino acid sequence of SEQ ID NO: 25.

12. The method of claim 1, wherein the HCVR comprises HCDR1, HCDR2 and HCDR3 of a heavy chain comprising the amino acid sequence of SEQ ID NO: 4; and the LCVR comprises LCDR1, LCDR2, and LCDR3 of a light chain comprising the amino acid sequence of SEQ ID NO: 5.

13. The method of claim 1, wherein the HCVR comprises an HCDR1 comprising the amino acid sequence of SEQ ID NO: 27, an HCDR2 comprising the amino acid sequence of SEQ ID NO: 28, and an HCDR3 comprising the amino acid sequence of SEQ ID NO:29; and the LCVR comprises an LCDR1 comprising the amino acid sequence of SEQ ID NO: 30, an LCDR2 comprising the amino acid sequence of SEQ ID NO: 31, and an LCDR3 comprising the amino acid sequence of SEQ ID NO: 32.

14. The method of claim 1, wherein the HCVR comprises an HCDR1 comprising the amino acid sequence of SEQ ID NO: 33, an HCDR2 comprising the amino acid sequence of SEQ ID NO: 34, and an HCDR3 comprising the amino acid sequence of SEQ ID NO:35; and the LCVR comprises an LCDR1 comprising the amino acid sequence of SEQ ID NO: 36, an LCDR2 comprising the amino acid sequence of SEQ ID NO: 37, and an LCDR3 comprising the amino acid sequence of SEQ ID NO: 38.

15. The method of claim 1, wherein the HCVR comprises an HCDR1 comprising the amino acid sequence of SEQ ID NO: 39, an HCDR2 comprising the amino acid sequence of SEQ ID NO: 40, and an HCDR3 comprising the amino acid sequence of SEQ ID NO:41; and the LCVR comprises an LCDR1 comprising the amino acid sequence of SEQ ID NO: 42, an LCDR2 comprising the amino acid sequence of SEQ ID NO: 43, and an LCDR3 comprising the amino acid sequence of SEQ ID NO: 45.

16. The method of claim 1, wherein the HCVR comprises an HCDR1 comprising the amino acid sequence of SEQ ID NO: 46, an HCDR2 comprising the amino acid sequence of SEQ ID NO: 47, and an HCDR3 comprising the amino acid sequence of SEQ ID NO:48; and the LCVR comprises an LCDR1 comprising the amino acid sequence of SEQ ID NO: 49, an LCDR2 comprising the amino acid sequence of SEQ ID NO: 50, and an LCDR3 comprising the amino acid sequence of SEQ ID NO: 51.

17. The method of claim 1, wherein the HCVR comprises an HCDR1 comprising the amino acid sequence of SEQ ID NO: 52, an HCDR2 comprising the amino acid sequence of SEQ ID NO: 53, and an HCDR3 comprising the amino acid sequence of SEQ ID NO: 54; and the LCVR comprises an LCDR1 comprising the amino acid sequence of SEQ ID NO: 55, an LCDR2 comprising the amino acid sequence of SEQ ID NO: 56, and an LCDR3 comprising the amino acid sequence of SEQ ID NO: 57.

18. The method of claim 1, wherein the HCVR comprises an HCDR1 comprising the amino acid sequence of SEQ ID NO: 58, an HCDR2 comprising the amino acid sequence of SEQ ID NO: 59, and an HCDR3 comprising the amino acid sequence of SEQ ID NO: 60; and the LCVR comprises an LCDR1 comprising the amino acid sequence of SEQ ID NO: 61, an LCDR2 comprising the amino acid sequence of SEQ ID NO: 62, and an LCDR3 comprising the amino acid sequence of SEQ ID NO: 63.

19. The method of claim 1, wherein the HCVR comprises an HCDR1 comprising the amino acid sequence of SEQ ID NO: 64, an HCDR2 comprising the amino acid sequence of SEQ ID NO: 65, and an HCDR3 comprising the amino acid sequence of SEQ ID NO: 66; and the LCVR comprises an LCDR1 comprising the amino acid sequence of SEQ ID NO: 67, an LCDR2 comprising the amino acid sequence of SEQ ID NO: 68, and an LCDR3 comprising the amino acid sequence of SEQ ID NO: 69.

20. The method of claim 1, wherein the HCVR comprises an HCDR1 comprising the amino acid sequence of SEQ ID NO: 70, an HCDR2 comprising the amino acid sequence of SEQ ID NO: 71, and an HCDR3 comprising the amino acid sequence of SEQ ID NO: 72; and the LCVR comprises an LCDR1 comprising the amino acid sequence of SEQ ID NO: 73, an LCDR2 comprising the amino acid sequence of SEQ ID NO: 74, and an LCDR3 comprising the amino acid sequence of SEQ ID NO: 75.

\* \* \* \* \*

SEQUENCE LISTING

<160> NUMBER OF SEQ ID NOS: 75

<210> SEQ ID NO 1
<211> LENGTH: 443
<212> TYPE: PRT
<213> ORGANISM: Artificial Sequence
<220> FEATURE:
<223> OTHER INFORMATION: Heavy chain

<400> SEQUENCE: 1

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Gly Leu Glu Trp Met
        35                  40                  45

Gly Tyr Ile Asn Pro Tyr Asn Asp Gly Thr Lys Tyr Asn Glu Asn Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Pro Phe Gly Asn Ala Met Asp Ile Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Ala Ala Gly Gly Pro Ser Val Phe Leu
225                 230                 235                 240
```

```
Phe Pro Pro Lys Pro Lys Asp Thr Leu Met Ile Ser Arg Thr Pro Glu
                245                 250                 255

Val Thr Cys Val Val Asp Val Ser Gln Glu Asp Pro Glu Val Gln
        260                 265                 270

Phe Asn Trp Tyr Val Asp Gly Val Glu Val His Asn Ala Lys Thr Lys
    275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu
        435                 440

<210> SEQ ID NO 2
<211> LENGTH: 444
<212> TYPE: PRT
<213> ORGANISM: Artificial Sequence
<220> FEATURE:
<223> OTHER INFORMATION: Heavy chain

<400> SEQUENCE: 2

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Gly Leu Glu Trp Met
        35                  40                  45

Gly Tyr Ile Asn Pro Tyr Asn Arg Gly Thr Lys Tyr Asn Glu Asn Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Pro Phe Gly Asn Ala Met Asp Ile Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160
```

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
        180                 185                 190

Ser Leu Gly Thr Lys Thr Tyr Thr Cys Asn Val Asp His Lys Pro Ser
    195                 200                 205

Asn Thr Lys Val Asp Lys Arg Val Glu Ser Lys Tyr Gly Pro Pro Cys
210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser Gln Glu Asp Pro Glu Val Gln
        260                 265                 270

Phe Asn Trp Tyr Val Asp Gly Val Glu Val His Asn Ala Lys Thr Lys
    275                 280                 285

Pro Arg Glu Glu Gln Phe Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
            325                 330                 335

Ala Lys Gly Gln Pro Arg Glu Pro Gln Val Tyr Thr Leu Pro Pro Ser
        340                 345                 350

Gln Glu Glu Met Thr Lys Asn Gln Val Ser Leu Thr Cys Leu Val Lys
    355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
            405                 410                 415

Glu Gly Asn Val Phe Ser Cys Ser Val Met His Glu Ala Leu His Asn
        420                 425                 430

His Tyr Thr Gln Lys Ser Leu Ser Leu Ser Leu Gly
    435                 440

<210> SEQ ID NO 3
<211> LENGTH: 214
<212> TYPE: PRT
<213> ORGANISM: Artificial Sequence
<220> FEATURE:
<223> OTHER INFORMATION: Light chain

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ser Ser Glu Asn Ile Tyr Arg Asn
            20                  25                  30

Leu Ala Trp Tyr Gln Gln Lys Pro Gly Lys Ala Pro Lys Leu Leu Ile
        35                  40                  45

Tyr Ala Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gly Ile Trp Gly Thr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 4
<211> LENGTH: 451
<212> TYPE: PRT
<213> ORGANISM: Homo sapiens
<220> FEATURE:
<223> OTHER INFORMATION: Heavy chain

<400> SEQUENCE: 4

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Val Val His Trp Val Arg Gln Ala Pro Gly Lys Gly Leu Glu Trp Val
        35                  40                  45

Gly Arg Ile Arg Leu Glu Thr His Gly Tyr Ala Ala Glu Tyr Ala Ala
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Val Glu Arg Ser Lys Ser Gly Phe Asp Asn Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

```
Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 5
<211> LENGTH: 217
<212> TYPE: PRT
<213> ORGANISM: Homo sapiens
<220> FEATURE:
<223> OTHER INFORMATION: Light chain

<400> SEQUENCE: 5

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Ser Val His Trp Tyr Gln Gln Leu Pro Gly Thr Ala Pro Lys Leu
        35                  40                  45

Leu Ile Tyr Gly Gln Ser Glu Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Trp Asp Ser Ser
                85                  90                  95

Gln Thr Leu Val Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125
```

```
Glu Leu Gln Ala Asn Lys Ala Thr Leu Val Cys Leu Ile Ser Asp Phe
    130                 135                 140
Tyr Pro Gly Ala Val Thr Val Ala Trp Lys Ala Asp Ser Ser Pro Val
145                 150                 155                 160
Lys Ala Gly Val Glu Thr Thr Thr Pro Ser Lys Gln Ser Asn Asn Lys
                165                 170                 175
Tyr Ala Ala Ser Ser Tyr Leu Ser Leu Thr Pro Glu Gln Trp Lys Ser
            180                 185                 190
His Arg Ser Tyr Ser Cys Gln Val Thr His Glu Gly Ser Thr Val Glu
                195                 200                 205
Lys Thr Val Ala Pro Thr Glu Cys Ser
    210                 215

<210> SEQ ID NO 6
<211> LENGTH: 7
<212> TYPE: PRT
<213> ORGANISM: Homo sapiens
<220> FEATURE:
<223> OTHER INFORMATION: Human BMP6 epitope motif

<400> SEQUENCE: 6

His Leu Met Asn Pro Glu Tyr
1               5

<210> SEQ ID NO 7
<211> LENGTH: 15
<212> TYPE: PRT
<213> ORGANISM: Homo sapiens
<220> FEATURE:
<223> OTHER INFORMATION: Human BMP6 epitope motif

<400> SEQUENCE: 7

Thr Gln Ser Gln Asp Val Ala Arg Val Ser Ser Ala Ser Asp Tyr
1               5                   10                  15

<210> SEQ ID NO 8
<211> LENGTH: 30
<212> TYPE: PRT
<213> ORGANISM: Homo sapiens
<220> FEATURE:
<223> OTHER INFORMATION: Human BMP6 epitope motif

<400> SEQUENCE: 8

Gln Gln Ser Arg Asn Arg Ser Thr Gln Ser Gln Asp Val Ala Arg Val
1               5                   10                  15
Ser Ser Ala Ser Asp Tyr Asn Ser Ser Glu Leu Lys Thr Ala
            20                  25                  30

<210> SEQ ID NO 9
<211> LENGTH: 7
<212> TYPE: PRT
<213> ORGANISM: Homo sapiens
<220> FEATURE:
<223> OTHER INFORMATION: Human BMP6 epitope motif

<400> SEQUENCE: 9

Gln Gln Ser Arg Asn Arg Ser
1               5

<210> SEQ ID NO 10
<211> LENGTH: 8
<212> TYPE: PRT
<213> ORGANISM: Homo sapiens
```

```
<220> FEATURE:
<223> OTHER INFORMATION: Human BMP6 epitope motif

<400> SEQUENCE: 10

Asn Ser Ser Glu Leu Lys Thr Ala
1               5

<210> SEQ ID NO 11
<211> LENGTH: 15
<212> TYPE: PRT
<213> ORGANISM: Homo sapiens
<220> FEATURE:
<223> OTHER INFORMATION: Human BMP6 epitope motif

<400> SEQUENCE: 11

Gln Gln Ser Arg Asn Arg Ser Thr Gln Ser Gln Asp Val Ala Arg
1               5                   10                  15

<210> SEQ ID NO 12
<211> LENGTH: 15
<212> TYPE: PRT
<213> ORGANISM: Homo sapiens
<220> FEATURE:
<223> OTHER INFORMATION: Human BMP6 epitope motif

<400> SEQUENCE: 12

Val Ser Ser Ala Ser Asp Tyr Asn Ser Ser Glu Leu Lys Thr Ala
1               5                   10                  15

<210> SEQ ID NO 13
<211> LENGTH: 26
<212> TYPE: PRT
<213> ORGANISM: Homo sapiens
<220> FEATURE:
<223> OTHER INFORMATION: Human BMP6 epitope motif

<400> SEQUENCE: 13

Ala Arg Val Ser Ser Ala Ser Asp Tyr Asn Ser Ser Glu Leu Lys Thr
1               5                   10                  15

Ala Cys Arg Lys His Glu Leu Tyr Val Ser
            20                  25

<210> SEQ ID NO 14
<211> LENGTH: 25
<212> TYPE: PRT
<213> ORGANISM: Homo sapiens
<220> FEATURE:
<223> OTHER INFORMATION: Human BMP6 epitope motif

<400> SEQUENCE: 14

Lys His Glu Leu Tyr Val Ser Phe Gln Asp Leu Gly Trp Gln Asp Trp
1               5                   10                  15

Ile Ile Ala Pro Lys Gly Tyr Ala Ala
            20                  25

<210> SEQ ID NO 15
<211> LENGTH: 26
<212> TYPE: PRT
<213> ORGANISM: Homo sapiens
<220> FEATURE:
<223> OTHER INFORMATION: Human BMP6 epitope motif

<400> SEQUENCE: 15

Gly Trp Gln Asp Trp Ile Ile Ala Pro Lys Gly Tyr Ala Ala Asn Tyr
1               5                   10                  15
```

Cys Asp Gly Glu Cys Ser Phe Pro Leu Asn
            20                  25

<210> SEQ ID NO 16
<211> LENGTH: 28
<212> TYPE: PRT
<213> ORGANISM: Homo sapiens
<220> FEATURE:
<223> OTHER INFORMATION: Human BMP6 epitope motif

<400> SEQUENCE: 16

Gly Tyr Ala Ala Asn Tyr Cys Asp Gly Glu Cys Ser Phe Pro Leu Asn
1               5                   10                  15

Ala His Met Asn Ala Thr Asn His Ala Ile Val Gln
            20                  25

<210> SEQ ID NO 17
<211> LENGTH: 35
<212> TYPE: PRT
<213> ORGANISM: Homo sapiens
<220> FEATURE:
<223> OTHER INFORMATION: Human BMP6 epitope motif

<400> SEQUENCE: 17

Phe Pro Leu Asn Ala His Met Asn Ala Thr Asn His Ala Ile Val Gln
1               5                   10                  15

Thr Leu Val His Leu Met Asn Pro Glu Tyr Val Pro Lys Pro Cys Cys
            20                  25                  30

Ala Pro Thr
        35

<210> SEQ ID NO 18
<211> LENGTH: 17
<212> TYPE: PRT
<213> ORGANISM: Homo sapiens
<220> FEATURE:
<223> OTHER INFORMATION: Human BMP6 epitope motif

<400> SEQUENCE: 18

Val Pro Lys Pro Cys Cys Ala Pro Thr Lys Leu Asn Ala Ile Ser Val
1               5                   10                  15

Leu

<210> SEQ ID NO 19
<211> LENGTH: 21
<212> TYPE: PRT
<213> ORGANISM: Homo sapiens
<220> FEATURE:
<223> OTHER INFORMATION: Human BMP6 epitope motif

<400> SEQUENCE: 19

Asn Ala Ile Ser Val Leu Tyr Phe Asp Asp Asn Ser Asn Val Ile Leu
1               5                   10                  15

Lys Lys Tyr Arg Asn
            20

<210> SEQ ID NO 20
<211> LENGTH: 10
<212> TYPE: PRT
<213> ORGANISM: Artificial Sequence
<220> FEATURE:
<223> OTHER INFORMATION: Synthetic Construct

<400> SEQUENCE: 20

```
Gly Tyr Thr Phe Thr Ser Tyr Ala Met His
1               5                   10
```

<210> SEQ ID NO 21
<211> LENGTH: 17
<212> TYPE: PRT
<213> ORGANISM: Artificial Sequence
<220> FEATURE:
<223> OTHER INFORMATION: Synthetic Construct

<400> SEQUENCE: 21

```
Tyr Ile Asn Pro Tyr Asn Asp Gly Thr Lys Tyr Asn Glu Asn Phe Lys
1               5                   10                  15
Gly
```

<210> SEQ ID NO 22
<211> LENGTH: 9
<212> TYPE: PRT
<213> ORGANISM: Artificial Sequence
<220> FEATURE:
<223> OTHER INFORMATION: Synthetic Construct

<400> SEQUENCE: 22

```
Arg Pro Phe Gly Asn Ala Met Asp Ile
1               5
```

<210> SEQ ID NO 23
<211> LENGTH: 11
<212> TYPE: PRT
<213> ORGANISM: Artificial Sequence
<220> FEATURE:
<223> OTHER INFORMATION: Synthetic Construct

<400> SEQUENCE: 23

```
Arg Ser Ser Glu Asn Ile Tyr Arg Asn Leu Ala
1               5                   10
```

<210> SEQ ID NO 24
<211> LENGTH: 7
<212> TYPE: PRT
<213> ORGANISM: Artificial Sequence
<220> FEATURE:
<223> OTHER INFORMATION: Synthetic Construct

<400> SEQUENCE: 24

```
Ala Ala Thr Asn Leu Ala Asp
1               5
```

<210> SEQ ID NO 25
<211> LENGTH: 9
<212> TYPE: PRT
<213> ORGANISM: Artificial Sequence
<220> FEATURE:
<223> OTHER INFORMATION: Synthetic Construct

<400> SEQUENCE: 25

```
Gln Gly Ile Trp Gly Thr Pro Leu Thr
1               5
```

<210> SEQ ID NO 26
<211> LENGTH: 17
<212> TYPE: PRT
<213> ORGANISM: Artificial Sequence
<220> FEATURE:
<223> OTHER INFORMATION: Synthetic Construct

<400> SEQUENCE: 26

Tyr Ile Asn Pro Tyr Asn Arg Gly Thr Lys Tyr Asn Glu Asn Phe Lys
1               5                   10                  15

Gly

<210> SEQ ID NO 27
<211> LENGTH: 5
<212> TYPE: PRT
<213> ORGANISM: Artificial Sequence
<220> FEATURE:
<223> OTHER INFORMATION: Synthetic Construct

<400> SEQUENCE: 27

Ser Tyr Val Val His
1               5

<210> SEQ ID NO 28
<211> LENGTH: 19
<212> TYPE: PRT
<213> ORGANISM: Artificial Sequence
<220> FEATURE:
<223> OTHER INFORMATION: Synthetic Construct

<400> SEQUENCE: 28

Arg Ile Arg Leu Glu Thr His Gly Tyr Ala Ala Glu Tyr Ala Ala Ser
1               5                   10                  15

Val Lys Gly

<210> SEQ ID NO 29
<211> LENGTH: 10
<212> TYPE: PRT
<213> ORGANISM: Artificial Sequence
<220> FEATURE:
<223> OTHER INFORMATION: Synthetic Construct

<400> SEQUENCE: 29

Val Glu Arg Ser Lys Ser Gly Phe Asp Asn
1               5                   10

<210> SEQ ID NO 30
<211> LENGTH: 14
<212> TYPE: PRT
<213> ORGANISM: Artificial Sequence
<220> FEATURE:
<223> OTHER INFORMATION: Synthetic Construct

<400> SEQUENCE: 30

Thr Gly Ser Ser Ser Asn Ile Gly Ala Gly Tyr Ser Val His
1               5                   10

<210> SEQ ID NO 31
<211> LENGTH: 7
<212> TYPE: PRT
<213> ORGANISM: Artificial Sequence
<220> FEATURE:
<223> OTHER INFORMATION: Synthetic Construct

<400> SEQUENCE: 31

Gly Gln Ser Glu Arg Pro Ser
1               5

<210> SEQ ID NO 32
<211> LENGTH: 11
<212> TYPE: PRT
<213> ORGANISM: Artificial Sequence
<220> FEATURE:

<223> OTHER INFORMATION: Synthetic Construct

<400> SEQUENCE: 32

Gln Ser Trp Asp Ser Ser Gln Thr Leu Val Val
1               5                   10

<210> SEQ ID NO 33
<211> LENGTH: 7
<212> TYPE: PRT
<213> ORGANISM: Artificial Sequence
<220> FEATURE:
<223> OTHER INFORMATION: Synthetic Construct

<400> SEQUENCE: 33

Gly Phe Thr Phe Ser Ser Tyr
1               5

<210> SEQ ID NO 34
<211> LENGTH: 8
<212> TYPE: PRT
<213> ORGANISM: Artificial Sequence
<220> FEATURE:
<223> OTHER INFORMATION: Synthetic Construct

<400> SEQUENCE: 34

Arg Leu Glu Thr His Gly Tyr Ala
1               5

<210> SEQ ID NO 35
<211> LENGTH: 10
<212> TYPE: PRT
<213> ORGANISM: Artificial Sequence
<220> FEATURE:
<223> OTHER INFORMATION: Synthetic Construct

<400> SEQUENCE: 35

Val Glu Arg Ser Lys Ser Gly Phe Asp Asn
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Synthetic Construct

<400> SEQUENCE: 36

Ser Ser Ser Asn Ile Gly Ala Gly Tyr Ser
1               5                   10

<210> SEQ ID NO 37
<211> LENGTH: 3
<212> TYPE: PRT
<213> ORGANISM: Artificial Sequence
<220> FEATURE:
<223> OTHER INFORMATION: Synthetic Construct

<400> SEQUENCE: 37

Gly Gln Ser
1

<210> SEQ ID NO 38
<211> LENGTH: 8
<212> TYPE: PRT
<213> ORGANISM: Artificial Sequence
<220> FEATURE:
<223> OTHER INFORMATION: Synthetic Construct

```
<400> SEQUENCE: 38

Trp Asp Ser Ser Gln Thr Leu Val
1               5

<210> SEQ ID NO 39
<211> LENGTH: 5
<212> TYPE: PRT
<213> ORGANISM: Artificial Sequence
<220> FEATURE:
<223> OTHER INFORMATION: Synthetic Construct

<400> SEQUENCE: 39

Ser Tyr Val Val His
1               5

<210> SEQ ID NO 40
<211> LENGTH: 19
<212> TYPE: PRT
<213> ORGANISM: Artificial Sequence
<220> FEATURE:
<223> OTHER INFORMATION: Synthetic Construct

<400> SEQUENCE: 40

Arg Ile Lys Arg Glu Ser Ser Tyr Thr Thr Met Tyr Ala Ala Pro
1               5                   10                  15

Val Lys Gly

<210> SEQ ID NO 41
<211> LENGTH: 10
<212> TYPE: PRT
<213> ORGANISM: Artificial Sequence
<220> FEATURE:
<223> OTHER INFORMATION: Synthetic Construct

<400> SEQUENCE: 41

Val Glu Arg Ser Lys Ser Gly Phe Asp Asn
1               5                   10

<210> SEQ ID NO 42
<211> LENGTH: 14
<212> TYPE: PRT
<213> ORGANISM: Artificial Sequence
<220> FEATURE:
<223> OTHER INFORMATION: Synthetic Construct

<400> SEQUENCE: 42

Thr Gly Ser Ser Ser Asn Ile Gly Ala Gly Tyr Ser Val His
1               5                   10

<210> SEQ ID NO 43
<211> LENGTH: 7
<212> TYPE: PRT
<213> ORGANISM: Artificial Sequence
<220> FEATURE:
<223> OTHER INFORMATION: Synthetic Construct

<400> SEQUENCE: 43

Gly Gln Ser Glu Arg Pro Ser
1               5

<210> SEQ ID NO 44
<211> LENGTH: 12
<212> TYPE: DNA
<213> ORGANISM: Artificial Sequence
<220> FEATURE:
```

<223> OTHER INFORMATION: Synthetic Construct

<400> SEQUENCE: 44
aaatttcccg gg                                                            12

<210> SEQ ID NO 45
<211> LENGTH: 11
<212> TYPE: PRT
<213> ORGANISM: Artificial Sequence
<220> FEATURE:
<223> OTHER INFORMATION: Synthetic Construct

<400> SEQUENCE: 45

Gln Ser Trp Asp Ser Ser Gln Thr Leu Val Val
1               5                   10

<210> SEQ ID NO 46
<211> LENGTH: 7
<212> TYPE: PRT
<213> ORGANISM: Artificial Sequence
<220> FEATURE:
<223> OTHER INFORMATION: Synthetic Construct

<400> SEQUENCE: 46

Gly Phe Thr Phe Ser Ser Tyr
1               5

<210> SEQ ID NO 47
<211> LENGTH: 8
<212> TYPE: PRT
<213> ORGANISM: Artificial Sequence
<220> FEATURE:
<223> OTHER INFORMATION: Synthetic Construct

<400> SEQUENCE: 47

Lys Arg Glu Ser Ser Ser Tyr Thr
1               5

<210> SEQ ID NO 48
<211> LENGTH: 10
<212> TYPE: PRT
<213> ORGANISM: Artificial Sequence
<220> FEATURE:
<223> OTHER INFORMATION: Synthetic Construct

<400> SEQUENCE: 48

Val Glu Arg Ser Lys Ser Gly Phe Asp Asn
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Synthetic Construct

<400> SEQUENCE: 49

Ser Ser Ser Asn Ile Gly Ala Gly Tyr Ser
1               5                   10

<210> SEQ ID NO 50
<211> LENGTH: 3
<212> TYPE: PRT
<213> ORGANISM: Artificial Sequence
<220> FEATURE:
<223> OTHER INFORMATION: Synthetic Construct

```
<400> SEQUENCE: 50

Gly Gln Ser
1

<210> SEQ ID NO 51
<211> LENGTH: 8
<212> TYPE: PRT
<213> ORGANISM: Artificial Sequence
<220> FEATURE:
<223> OTHER INFORMATION: Synthetic Construct

<400> SEQUENCE: 51

Trp Asp Ser Ser Gln Thr Leu Val
1               5

<210> SEQ ID NO 52
<211> LENGTH: 5
<212> TYPE: PRT
<213> ORGANISM: Artificial Sequence
<220> FEATURE:
<223> OTHER INFORMATION: Synthetic Construct

<400> SEQUENCE: 52

Ser Tyr Val Val His
1               5

<210> SEQ ID NO 53
<211> LENGTH: 19
<212> TYPE: PRT
<213> ORGANISM: Artificial Sequence
<220> FEATURE:
<223> OTHER INFORMATION: Synthetic Construct

<400> SEQUENCE: 53

Arg Thr Arg His Ser Asp Met Gly Tyr Ala Thr Ser Tyr Ala Ala Pro
1               5                   10                  15

Val Lys Gly

<210> SEQ ID NO 54
<211> LENGTH: 10
<212> TYPE: PRT
<213> ORGANISM: Artificial Sequence
<220> FEATURE:
<223> OTHER INFORMATION: Synthetic Construct

<400> SEQUENCE: 54

Val Glu Arg Ser Lys Ser Gly Phe Asp Asn
1               5                   10

<210> SEQ ID NO 55
<211> LENGTH: 14
<212> TYPE: PRT
<213> ORGANISM: Artificial Sequence
<220> FEATURE:
<223> OTHER INFORMATION: Synthetic Construct

<400> SEQUENCE: 55

Thr Gly Ser Ser Ser Asn Ile Gly Ala Gly Tyr Ser Val His
1               5                   10

<210> SEQ ID NO 56
<211> LENGTH: 7
<212> TYPE: PRT
<213> ORGANISM: Artificial Sequence
<220> FEATURE:
<223> OTHER INFORMATION: Synthetic Construct
```

```
<400> SEQUENCE: 56

Gly Gln Ser Glu Arg Pro Ser
1               5

<210> SEQ ID NO 57
<211> LENGTH: 11
<212> TYPE: PRT
<213> ORGANISM: Artificial Sequence
<220> FEATURE:
<223> OTHER INFORMATION: Synthetic Construct

<400> SEQUENCE: 57

Gln Ser Trp Asp Ser Ser Gln Thr Leu Val Val
1               5                   10

<210> SEQ ID NO 58
<211> LENGTH: 7
<212> TYPE: PRT
<213> ORGANISM: Artificial Sequence
<220> FEATURE:
<223> OTHER INFORMATION: Synthetic Construct

<400> SEQUENCE: 58

Gly Phe Thr Phe Ser Ser Tyr
1               5

<210> SEQ ID NO 59
<211> LENGTH: 8
<212> TYPE: PRT
<213> ORGANISM: Artificial Sequence
<220> FEATURE:
<223> OTHER INFORMATION: Synthetic Construct

<400> SEQUENCE: 59

Arg His Ser Asp Met Gly Tyr Ala
1               5

<210> SEQ ID NO 60
<211> LENGTH: 10
<212> TYPE: PRT
<213> ORGANISM: Artificial Sequence
<220> FEATURE:
<223> OTHER INFORMATION: Synthetic Construct

<400> SEQUENCE: 60

Val Glu Arg Ser Lys Ser Gly Phe Asp Asn
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Synthetic Construct

<400> SEQUENCE: 61

Ser Ser Ser Asn Ile Gly Ala Gly Tyr Ser
1               5                   10

<210> SEQ ID NO 62
<211> LENGTH: 3
<212> TYPE: PRT
<213> ORGANISM: Artificial Sequence
<220> FEATURE:
<223> OTHER INFORMATION: Synthetic Construct
```

```
<400> SEQUENCE: 62

Gly Gln Ser
1

<210> SEQ ID NO 63
<211> LENGTH: 8
<212> TYPE: PRT
<213> ORGANISM: Artificial Sequence
<220> FEATURE:
<223> OTHER INFORMATION: Synthetic Construct

<400> SEQUENCE: 63

Trp Asp Ser Ser Gln Thr Leu Val
1               5

<210> SEQ ID NO 64
<211> LENGTH: 5
<212> TYPE: PRT
<213> ORGANISM: Artificial Sequence
<220> FEATURE:
<223> OTHER INFORMATION: Synthetic Construct

<400> SEQUENCE: 64

Ser Tyr Val Val His
1               5

<210> SEQ ID NO 65
<211> LENGTH: 19
<212> TYPE: PRT
<213> ORGANISM: Artificial Sequence
<220> FEATURE:
<223> OTHER INFORMATION: Synthetic Construct

<400> SEQUENCE: 65

Arg Ile Lys Asp His Lys Gln Gly Tyr Thr Thr Ala Tyr Ala Ala Ser
1               5                   10                  15

Val Lys Gly

<210> SEQ ID NO 66
<211> LENGTH: 10
<212> TYPE: PRT
<213> ORGANISM: Artificial Sequence
<220> FEATURE:
<223> OTHER INFORMATION: Synthetic Construct

<400> SEQUENCE: 66

Val Glu Arg Ser Lys Ser Gly Phe Asp Asn
1               5                   10

<210> SEQ ID NO 67
<211> LENGTH: 14
<212> TYPE: PRT
<213> ORGANISM: Artificial Sequence
<220> FEATURE:
<223> OTHER INFORMATION: Synthetic Construct

<400> SEQUENCE: 67

Thr Gly Ser Ser Ser Asn Ile Gly Ala Gly Tyr Ser Val His
1               5                   10

<210> SEQ ID NO 68
<211> LENGTH: 7
<212> TYPE: PRT
<213> ORGANISM: Artificial Sequence
<220> FEATURE:
<223> OTHER INFORMATION: Synthetic Construct
```

<400> SEQUENCE: 68

Gly Ser Ser Glu Arg Pro Ser
1               5

<210> SEQ ID NO 69
<211> LENGTH: 11
<212> TYPE: PRT
<213> ORGANISM: Artificial Sequence
<220> FEATURE:
<223> OTHER INFORMATION: Synthetic Construct

<400> SEQUENCE: 69

Gln Ser Trp Asp Ser Ser Gln Thr Leu Val Val
1               5                   10

<210> SEQ ID NO 70
<211> LENGTH: 7
<212> TYPE: PRT
<213> ORGANISM: Artificial Sequence
<220> FEATURE:
<223> OTHER INFORMATION: Synthetic Construct

<400> SEQUENCE: 70

Gly Phe Thr Phe Ser Ser Tyr
1               5

<210> SEQ ID NO 71
<211> LENGTH: 8
<212> TYPE: PRT
<213> ORGANISM: Artificial Sequence
<220> FEATURE:
<223> OTHER INFORMATION: Synthetic Construct

<400> SEQUENCE: 71

Lys Asp His Lys Gln Gly Tyr Thr
1               5

<210> SEQ ID NO 72
<211> LENGTH: 10
<212> TYPE: PRT
<213> ORGANISM: Artificial Sequence
<220> FEATURE:
<223> OTHER INFORMATION: Synthetic Construct

<400> SEQUENCE: 72

Val Glu Arg Ser Lys Ser Gly Phe Asp Asn
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Synthetic Construct

<400> SEQUENCE: 73

Ser Ser Ser Asn Ile Gly Ala Gly Tyr Ser
1               5                   10

<210> SEQ ID NO 74
<211> LENGTH: 3
<212> TYPE: PRT
<213> ORGANISM: Artificial Sequence
<220> FEATURE:
<223> OTHER INFORMATION: Synthetic Construct

```
<400> SEQUENCE: 74

Gly Ser Ser
1

<210> SEQ ID NO 75
<211> LENGTH: 8
<212> TYPE: PRT
<213> ORGANISM: Artificial Sequence
<220> FEATURE:
<223> OTHER INFORMATION: Synthetic Construct

<400> SEQUENCE: 75

Trp Asp Ser Ser Gln Thr Leu Val
1               5
```